United States Patent
Hansen et al.

(10) Patent No.: US 12,329,673 B2
(45) Date of Patent: Jun. 17, 2025

(54) ACCELEROMETER IN MONITOR DEVICE

(71) Applicant: Coloplast A/S, Humlebaek (DK)

(72) Inventors: Jais Ask Hansen, Jaegerspris (DK); Lars Molzen, Kongens Lyngby (DK)

(73) Assignee: Coloplast A/S, Humlebaek (DK)

(*) Notice: Subject to any disclaimer, the term of this patent is extended or adjusted under 35 U.S.C. 154(b) by 727 days.

(21) Appl. No.: 17/606,060

(22) PCT Filed: Apr. 27, 2020

(86) PCT No.: PCT/DK2020/050116
§ 371 (c)(1),
(2) Date: Oct. 25, 2021

(87) PCT Pub. No.: WO2020/216429
PCT Pub. Date: Oct. 29, 2020

(65) Prior Publication Data
US 2022/0241105 A1    Aug. 4, 2022

(30) Foreign Application Priority Data

Apr. 26, 2019 (DK) .................................. 2019 70262

(51) Int. Cl.
*A61F 5/44* (2006.01)
*A61B 5/00* (2006.01)

(52) U.S. Cl.
CPC ............ *A61F 5/4404* (2013.01); *A61B 5/441* (2013.01); *A61B 5/742* (2013.01);
(Continued)

(58) Field of Classification Search
CPC ........ A61F 5/4404; A61F 5/443; A61F 5/445; A61B 5/441; A61B 5/742;
(Continued)

(56) References Cited

U.S. PATENT DOCUMENTS 6,171,289 B1    1/2001 Millot et al.
6,785,975 B1    9/2004 Campbell et al.
(Continued)

FOREIGN PATENT DOCUMENTS

CN    105377200 B    1/2018
JP    2009528519 A    8/2009
(Continued)

*Primary Examiner* — Philip R Wiest
*Assistant Examiner* — Brandon W. Levy
(74) *Attorney, Agent, or Firm* — Coloplast Corp., Coloplast A/S; Nick Baumann

(57) ABSTRACT

A monitor device (6) for coupling to a sensor assembly of an ostomy appliance is disclosed. The monitor device comprises a housing, a processor arranged in said housing, and an appliance interface configured for coupling the monitor device to the sensor assembly. The appliance interface comprises a plurality of terminals for connecting with a plurality of electrodes of the sensor assembly. Further, the monitor device comprises a three-axis accelerometer (540) configured to generate a position signal. Further, a method for determining a rotational offset of a sensor assembly relative to an ostomy and a system comprising a monitor device and a sensor assembly is disclosed.

24 Claims, 21 Drawing Sheets

(52) U.S. Cl.
CPC . *A61B 2562/0219* (2013.01); *A61B 2562/029* (2013.01); *A61B 2562/063* (2013.01)

(58) Field of Classification Search
CPC ...... A61B 2562/0219; A61B 2562/029; A61B 2562/063; A61B 5/4851; A61B 5/746; A61B 5/1123; G16H 40/67; G16H 20/30
See application file for complete search history.

(56) References Cited

U.S. PATENT DOCUMENTS

| | | | |
|---|---|---|---|
| 9,289,165 B2 | 3/2016 | Soykan et al. | |
| 9,352,152 B2 | 5/2016 | Lindenthaler et al. | |
| 10,278,857 B2 | 5/2019 | Hansen et al. | |
| 11,596,670 B2 | 3/2023 | Jones et al. | |
| 2009/0319221 A1* | 12/2009 | Kahn | G06F 3/0346 702/141 |
| 2010/0030167 A1 | 2/2010 | Thirstrup et al. | |
| 2013/0324952 A1 | 12/2013 | Krystek et al. | |
| 2014/0235171 A1* | 8/2014 | Molettiere | A61B 5/486 455/41.2 |
| 2015/0119728 A1* | 4/2015 | Blackadar | G16H 20/30 600/483 |
| 2017/0140103 A1* | 5/2017 | Angelides | A61F 5/4404 |
| 2020/0000624 A1* | 1/2020 | Gibbons | A61B 5/444 |

FOREIGN PATENT DOCUMENTS

| | | |
|---|---|---|
| RU | 2480254 C2 | 4/2013 |
| RU | 2596054 C2 | 8/2016 |
| RU | 2648225 C2 | 3/2018 |
| WO | 2007098762 A1 | 9/2007 |
| WO | 2013064852 A1 | 5/2013 |
| WO | 2018183931 A1 | 10/2018 |
| WO | 2019174693 A1 | 9/2019 |

\* cited by examiner

ACCELEROMETER IN MONITOR DEVICE

The present disclosure relates to a monitor device for a sensor assembly comprising an accelerometer for determining a spatial orientation. Further, the present disclosure relates to a method for determining a rotational offset of a sensor assembly relative to an ostomy.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
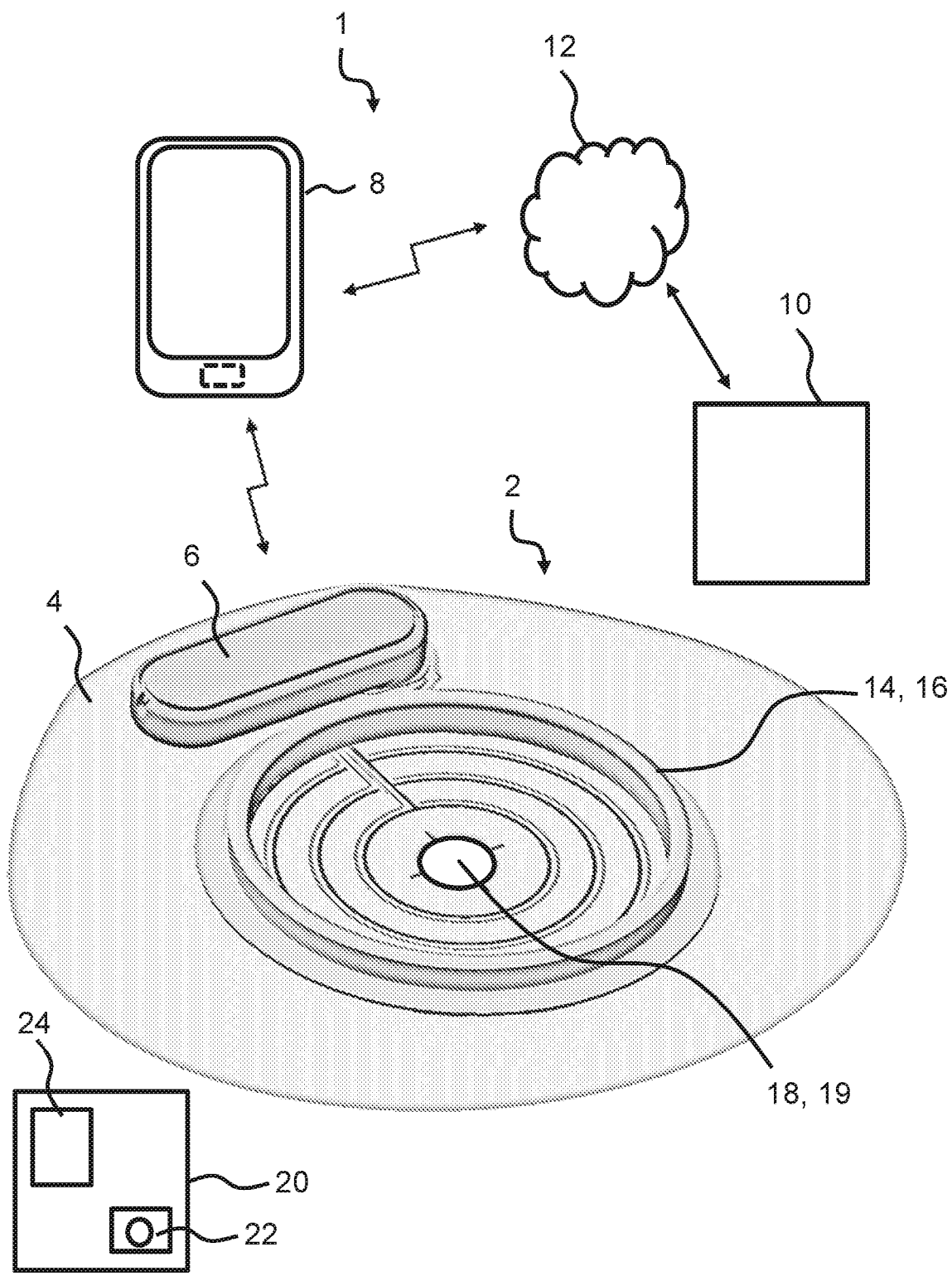
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," "liquids," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

A radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure provides a monitor device for coupling to a sensor assembly of an ostomy appliance, a method for determining a rotational offset of a sensor assembly relative to an ostomy, and an ostomy system comprising a sensor assembly and a monitor device.

In a first aspect of the invention, a monitor device for coupling to a sensor assembly of an ostomy appliance is disclosed. The monitor device comprises a housing, a processor arranged in the housing, and an appliance interface configured for coupling the monitor device to the sensor assembly. The appliance interface comprises a plurality of terminals for connecting with a plurality of electrodes of the sensor assembly. Further, the monitor device comprises a three-axis accelerometer configured to generate a position signal. The three-axis accelerometer is capable of assessing/measuring acceleration in a three-dimensional space spanned by an x-axis, a y-axis, and a z-axis being mutually orthogonal. In the following, the accelerometer is said to comprise an x-axis, a y-axis, and z-axis. Thus, the axes of the accelerometer span a Cartesian coordinate system. In embodiments, the accelerometer is a two-axis accelerometer.

The present disclosure relates to an ostomy system and devices thereof, such as an ostomy appliance, a base plate for an ostomy appliance, a sensor patch for application to a baseplate, a monitor device, and optionally one or more accessory devices. Further, methods related to the ostomy system and devices thereof are disclosed. An accessory device (also referred to as an external device) can be a mobile phone or other handheld device. In embodiments, an accessory device is a personal electronic device, e.g. a wearable, such as a watch or other wrist-worn electronic device. An accessory device can be a docking station. In embodiments, the docking station is configured to electrically and/or mechanically couple the monitor device to the docking station. In embodiments, the docking station is configured for charging a battery of the monitor device and/or configured for transferring data between the monitor device and the docking station. The ostomy system can comprise a server device. In embodiments, the server device is operated and/or controlled by the ostomy appliance manufacturer and/or a service centre.

The present disclosure provides an ostomy system and devices thereof, such as an ostomy appliance, a base plate for an ostomy appliance, a sensor patch for application to a base plate, a monitor device, and optionally one or more accessory devices which either alone or together facilitate reliable determination of the nature, severity, and rapidness of moisture propagation in the adhesive material provided for attaching the base plate and/or sensor patch to the skin surface of a user. Depending on the nature of the pattern of moisture propagation in the adhesive, the ostomy system and devices thereof enable providing information to the user about the type of failure, and in turn enable providing an indication to the user of the severity and thus the remaining time frame for replacing the ostomy appliance without experiencing severe leakage and/or skin damage.

In embodiments, the ostomy appliance comprises a base plate and an ostomy pouch (also referred to as an ostomy bag). The ostomy appliance can be a colostomy appliance, an ileostomy appliance, or a urostomy appliance. In embodiments, the ostomy appliance is a two-part ostomy appliance, i.e. the base plate and the ostomy pouch are releasably coupled e.g. with a mechanical and/or an adhesive coupling, e.g. to allow that a plurality of ostomy pouches can be utilized (exchanged) with one base plate. Further, a two-part ostomy appliance can facilitate correct application of the base plate to skin, e.g. to an improved user sight of the stomal region. In embodiments, the ostomy appliance is a one-part ostomy appliance, i.e. the base plate and the ostomy pouch are fixedly attached to each other. The base plate is configured for coupling to a user's stoma and/or skin surrounding the stoma, such as a peristomal skin area.

In embodiments, the ostomy appliance includes a base plate, such as a monolithic, one-piece base plate, e.g. integrated with a sensor assembly part, or a separate sensor assembly part, such as a sensor assembly part to be subsequently applied to a base plate. In embodiments, the sensor assembly part is a sensor patch for application to the base plate, such as the proximal surface of the base plate. Thereby, an arbitrary base plate, such as a conventional base plate, can achieve the features as described herein. Features as described with respect to sensing/monitoring capabilities of the base plate herein can be provided by a sensor assembly of a sensor patch to be applied to a base plate, e.g. by the user, and vice versa. In embodiments, the sensor patch is adapted to adhere to a base plate.

In embodiments, a method of attaching a base plate having sensing capabilities, e.g. through the provision of a sensor patch, to a user's stoma and/or skin surrounding the stoma, such as the peristomal skin area, comprises attaching the sensor patch to a base plate and attaching the base plate, i.e. together with the attached sensor patch, to the user's stoma and/or skin surrounding the stoma, such as the peristomal skin area. Alternatively, the method of attaching the base plate to the user's stoma and/or skin surrounding the stoma comprises attaching the sensor patch to the user's stoma and/or skin surrounding the stoma and attaching the base plate to the user's stoma and/or skin surrounding the stoma above the attached sensor patch, i.e. on a distal surface of the sensor patch.

In embodiments, the base plate and/or the sensor patch comprises a first adhesive layer with a proximal side configured for attachment of the base plate and/or the sensor patch to the skin surface of a user. In embodiments, the first adhesive layer has a stomal opening, such as a first adhesive stomal opening, with a centre point.

In embodiments, the base plate and/or sensor patch comprises a plurality of electrodes including a first leakage electrode, a second leakage electrode, and a third leakage electrode provided in an electrode assembly of a sensor assembly. In embodiments, the plurality of electrodes is configured to detect presence of liquid, such as output, on the proximal side of the first adhesive layer and/or moisture content in the first adhesive layer. In embodiments, the electrode assembly of the sensor assembly is configured to detect presence of liquid, such as output, on the proximal side of the first adhesive layer and/or moisture content in the first adhesive layer in a primary sensing zone and a secondary sensing zone, separate from the primary sensing zone. In embodiments, the primary sensing zone is arranged in a primary angle space from the centre point of the first adhesive layer, and/or the secondary sensing zone is arranged in a secondary angle space, separate from the primary angle space, from the centre point of the first adhesive layer. Alternatively or additionally, the primary sensing zone can be arranged in a primary radial space from the centre point of the first adhesive layer and the secondary sensing zone can be arranged in a secondary radial space from the centre point of the first adhesive layer. In embodiments, the electrode assembly of the sensor assembly is configured to detect presence of liquid, such as output, on the proximal side of the first adhesive layer and/or moisture content in the first adhesive layer in three or more sensing zones.

In embodiments, the monitor device comprises a housing, a processor, a memory, a first interface (also referred to as an appliance interface) connected to the processor and the memory, and a second interface connected to the processor. The first interface is configured for obtaining ostomy data from the base plate and/or the sensor patch coupled to the first interface. The ostomy data comprises primary ostomy data from a primary electrode set of the base plate and/or the sensor patch, and secondary ostomy data from a secondary electrode set of the base plate and/or the sensor patch. In embodiments, the processor is configured to: obtain primary parameter data based on the primary ostomy data; obtain secondary parameter data based on the secondary ostomy data; and detect presence of liquid on the proximal side of the first adhesive layer and/or moisture in the first adhesive layer in a primary sensing zone based on the primary parameter data. In embodiments, the primary sensing zone is arranged in a primary angle space from the centre point of the first adhesive layer and/or arranged in a primary radial space from the centre point of the first adhesive layer. Further, in embodiments, the processor is configured to detect presence of liquid on the proximal side of the first adhesive layer and/or moisture in the first adhesive layer in a secondary sensing zone based on the secondary parameter data. In embodiments, the secondary sensing zone is arranged in a secondary angle space from the centre point of the first adhesive layer and/or arranged in a secondary radial space from the centre point of the first adhesive layer. In embodiments, in accordance with a detection of presence of liquid and/or moisture in the primary sensing zone, the processor is configured to transmit a primary monitor signal comprising monitor data indicative of presence of liquid and/or moisture in the primary sensing zone via the second interface; and in accordance with a detection of presence of liquid and/or moisture in the secondary sensing zone, transmit a secondary monitor signal comprising monitor data indicative of presence of liquid and/or moisture in the secondary sensing zone via the second interface.

The base plate and/or the sensor patch comprises a first adhesive layer. During use, the first adhesive layer adheres to the user's skin (peristomal area) and/or to additional seals, such as sealing paste, sealing tape and/or sealing ring. Thus, in embodiments, the first adhesive layer is configured for attachment of the base plate and/or the sensor patch to the skin surface of a user.

In embodiments, the first adhesive layer has a stomal opening, such as a first adhesive stomal opening, with a centre point or is at least prepared for forming a stomal opening with a centre point. A base plate and/or a sensor patch according to the present disclosure enables detection of presence of liquid or output on the proximal side of the first adhesive layer (between a skin surface of the user, such as the peristomal skin area, and the proximal surface of the first adhesive layer).

In embodiments, the first adhesive layer is made of a first composition. In embodiments, the first composition comprises one or more polyisobutenes and/or styrene-isoprene-styrene. In embodiments, the first composition comprises one or more hydrocolloids. In embodiments, the first composition comprises one or more water soluble or water swellable hydrocolloids. In embodiments, the first composition is a pressure sensitive adhesive composition suitable for medical purposes comprising a rubbery elastomeric base and one or more water soluble or water swellable hydrocolloids. In embodiments, the first composition comprises one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. For example, the styrene copolymer can be a styrene-butadiene-styrene block copolymer or a styrene-isoprene-styrene block copolymer. Preferably, one or more styrene-isoprene-styrene (SIS) block type copolymers are employed. The amount of styrene block-copolymer can be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semi-synthetic hydrocolloids, and synthetic hydrocolloids. The first composition can comprise 20-60% hydrocolloids. A preferred hydrocolloid is carboxymethyl cellulose (CMC). Optionally, the first composition can contain other components, such as fillers, tackifiers, plasticizers, and/or other additives.

The first adhesive layer can have a substantially uniform thickness. The first adhesive layer can have a thickness in the range from 0.1 mm to 1.5 mm, e.g. in the range from 0.2 mm to 1.2 mm, such as 0.8 mm or 1.0 mm. The first adhesive layer can have a primary thickness in a primary part of the first adhesive layer, e.g. in a primary region within a primary radial distance or in a primary radial distance range from the centre point of the stomal opening. The primary thickness can be in the range from 0.2 mm to 1.5 mm, such as about 1.0 mm. The primary radial distance can be in the range from 20 mm to 50 mm, such as in the range from 25 mm to 35 mm, e.g. 30 mm. The first adhesive layer can have a secondary thickness in a secondary part of the first adhesive layer, e.g. in a secondary region outside a secondary radial distance or in a secondary radial distance range from the centre point of the stomal opening. The secondary thickness can be in the range from 0.2 mm to 1.0 mm, such as about 0.5 mm. The secondary radial distance can be in the range from 20 mm to 50 mm, such as in the range from 25 mm to 35 mm, e.g. 30 mm.

In embodiments, the base plate and/or the sensor patch comprises a second layer. In embodiments, the second layer is an adhesive layer. In embodiments, the second layer has a second radial extension that is larger than a first radial extension of the first adhesive layer at least in a first angular range of the base plate and/or the sensor patch. Accordingly, a part of a proximal surface of the second layer can be configured for attachment to the skin surface of a user. The part of a proximal surface of the second layer configured for attachment to the skin surface of a user is also denoted the skin attachment surface of the second adhesive layer. The second layer can have a stomal opening, such as a second layer stomal opening and/or a second adhesive stomal opening, with a centre point.

In embodiments, the second adhesive layer is made of a second composition. In embodiments, the second composition comprises one or more polyisobutenes and/or styrene-isoprene-styrene. In embodiments, the second composition comprises one or more hydrocolloids. In embodiments, the second composition comprises one or more water soluble or water swellable hydrocolloids. In embodiments, the second composition is a pressure sensitive adhesive composition suitable for medical purposes comprising a rubbery elastomeric base and one or more water soluble or water swellable hydrocolloids. In embodiments, the second composition comprises one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. For example, the styrene copolymer can be a styrene-butadiene-styrene block copolymer or a styrene-isoprene-styrene block copolymer. Preferably, one or more styrene-isoprene-styrene (SIS) block type copolymers are employed. The amount of styrene block-copolymer can be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids, and synthetic hydrocolloids. The second composition can comprise 20-60% hydrocolloids. A preferred hydrocolloid is carboxymethyl cellulose (CMC). Optionally, the second composition can contain other components, such as fillers, tackifiers, plasticizers, and/or other additives.

Different ratio of contents can change properties of the first and/or second adhesive layers. In embodiments, the second adhesive layer and the first adhesive layer have different properties. In embodiments, the second adhesive layer (second composition) and the first adhesive layer (first composition) have different ratios of polyisobutenes, styrene-isoprene-styrene, and/or hydrocolloids. For example, the second adhesive layer can provide a stronger attachment to the skin compared to attachment to the skin provided by the first adhesive layer. Alternatively, or additionally, the second adhesive layer can be thinner than the first adhesive layer. Alternatively, or additionally, the second adhesive layer can be less water and/or sweat absorbing than the first adhesive layer. Alternatively, or additionally, the second adhesive layer can be less mouldable than the first adhesive layer. In embodiments, the second adhesive layer provides a second barrier against leakage.

The second layer can have a substantially uniform thickness. The second layer can have a thickness in the range from 0.1 mm to 1.5 mm, e.g. in the range from 0.2 mm to 1.0 mm, such as 0.5 mm, 0.6 mm, or 0.7 mm.

Providing a base plate having sensing capabilities, e.g. through an incorporated sensor assembly or through a sensor patch comprising a sensor assembly, provides for an optimum or improved use of an ostomy appliance. In particular, it is facilitated that a base plate is not changed too late (leading to adhesive failure, leakage and/or skin damage), or at least that a user is informed that a leakage will happen, is happening, or has happened. Accordingly, the user or a health care professional is able to monitor and plan the use of the ostomy appliance.

In embodiments, the base plate and/or the sensor patch comprises one or more electrodes, such as a plurality of electrodes, such as two, three, four, five, six, seven or more electrodes. The sensor patch can be applied to the base plate, such as to provide the base plate with the one or more electrodes. In embodiments, the electrodes are provided in an electrode assembly. In embodiments, the electrode assembly is provided in a sensor assembly.

In embodiments, the electrodes, e.g. some or all the electrodes, are arranged between the first adhesive layer and the second adhesive layer. In embodiments, the electrodes are arranged in an electrode assembly, e.g. an electrode layer of a sensor assembly. In embodiments, an electrode comprises a connection part for connecting the electrodes to other components and/or interface terminals/terminal elements, such as for connecting the electrodes to a monitor device. In embodiments, an electrode comprises one or more conductor parts and/or one or more sensing parts. A conductor part can be considered part of an electrode connecting two or more sensing parts, and/or connecting a sensing part with a connection part of the respective electrode. A sensing part can be considered a part of the electrode being suitable for sensing, e.g. liquid, such as liquid content, and/or output, such as output resulting from a leakage, or an imminent leakage. The sensing part can be suitable for sensing e.g. by its shape, said shape potentially being circular, oval, or rectangular. Thus, the conductor part can conduct a signal arising from the sensing part. In embodiments, an electrode comprises alternating conductor parts and sensing parts. In embodiments, the electrode assembly is arranged between the first adhesive layer and the second adhesive layer. The base plate and/or the sensor patch, e.g. the electrode assembly, can comprise a first electrode, a second electrode and optionally a third electrode. The base plate and/or the sensor patch, e.g. the electrode assembly, can comprise a fourth electrode and/or a fifth electrode. The base plate and/or the sensor patch, e.g. the electrode assembly, optionally comprises a sixth electrode. In embodiments, the base plate and/or the sensor patch, e.g. the electrode assembly, comprises a ground electrode. The ground electrode can comprise a first electrode part. In embodiments, the first electrode part of the ground electrode forms a ground or reference for the first electrode. In embodiments, the first electrode part forms a closed loop. The ground electrode can comprise a second electrode part. In embodiments, the second electrode part of the ground electrode forms a ground or reference for the second electrode. The ground electrode can comprise a third electrode part. In embodiments, the third electrode part of the ground electrode forms a ground or reference for the third electrode. The ground electrode can comprise a fourth electrode part. In embodiments, the fourth electrode part of the ground electrode forms a ground or reference for the fourth electrode and/or the fifth electrode. In embodiments, the ground electrode is configured as or forms a (common) reference electrode for some or all of the other electrodes of the electrode assembly.

The electrodes are electrically conductive and can comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

In embodiments, the electrode assembly comprises a support layer, also denoted a support film. In embodiments, the sensor assembly comprises the electrode assembly and the support layer. One or more electrodes can be formed, e.g. printed, on the proximal side of the support layer. One or more electrodes can be formed, e.g. printed, on the distal side of the support layer. Thus, one or more electrodes can be arranged between the support layer and the first adhesive layer. The electrode assembly, such as the support layer of the electrode assembly, can have a stomal opening, such as an electrode assembly stomal opening and/or a support layer stomal opening, with a centre point. In embodiments, the support layer comprises polymeric (e.g. polyurethane, PTFE, PVDF) and/or ceramic (e.g. alumina, silica) materials. In one or more exemplary base plates and/or sensor patches, the support layer is made of thermoplastic polyurethane (TPU). The support layer material can be made of or comprise one or more of polyester, a thermoplastic elastomer (TPE), polyimide, polyimide, ethylene-vinyl acetate (EVA), polyurea, and silicones. Exemplary thermoplastic elastomers of the support layer are styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

Determination of moisture pattern types or angular leakage patterns is useful in helping to reduce the risk of a user experiencing leakage from an ostomy appliance. Further, determination of moisture pattern types and classification of operating states and/or leakage patterns of the ostomy appliance is further useful in helping reduce the risk of skin damage to a user.

In embodiments, the primary sensing zone of the base plate and/or the sensor patch is arranged in a primary angle space from the centre point of the first adhesive layer. In embodiments, the primary angle space spans a primary angle in the range from 45° to 315°, such as in the range from 45° to 135°. In embodiments, the primary angle depends on the number of angular sensing zones on the base plate and/or the sensor patch. For example, the primary angle can be about 180°±15°, e.g. for a base plate and/or a sensor patch with two or more sensing zones. The primary angle can be about 120°±15°, e.g. for a base plate and/or a sensor patch with two, three or more sensing zones. The primary angle can be about 90°±15°, e.g. for a base plate and/or a sensor patch with two, three, four or more sensing zones. The sensing zones are separate and non-overlapping.

Alternatively or additionally, the primary sensing zone can be arranged in a primary radial space from the centre point of the first adhesive layer. In embodiments, the primary radial space spans a primary radius in the range from 10-50 mm, such as in the range from 10-25 mm, such as in the range from 19-20 mm. In embodiments, the primary radius depends on the number of radial sensing zones on the base plate and/or the sensor patch.

In embodiments, the secondary sensing zone is arranged in a secondary angle space from the centre point of the first adhesive layer. In embodiments, the secondary angle space spans a secondary angle in the range from 45° to 315°, such as in the range from 45° to 135°. In embodiments, the secondary angle depends on the number of angular sensing zones on the base plate and/or the sensor patch. For example, the secondary angle can be about 180°±15°, e.g. for a base plate and/or a sensor patch with two or more sensing zones. The secondary angle can be about 120°±15°, e.g. for a base plate and/or a sensor patch with two, three or more sensing zones. The secondary angle can be about 90°±15°, e.g. for a base plate and/or a sensor patch with two, three, four or more sensing zones.

Alternatively or additionally, the secondary sensing zone can be arranged in a secondary radial space from the centre point of the first adhesive layer. In embodiments, the secondary radial space spans a secondary radius in the range from 15-50 mm, such as in the range from 20-30, such as in the range from 25-26 mm. In embodiments, the secondary radius depends on the number of radial sensing zones on the base plate and/or the sensor patch. In embodiments, the secondary radius is greater than the primary radius.

In embodiments, the plurality of electrodes is configured to detect presence of liquid on the proximal side in a tertiary sensing zone. In embodiments, the tertiary sensing zone is arranged in a tertiary angle space from the centre point of the first adhesive layer. In embodiments, the tertiary angle space spans a tertiary angle in the range from 45° to 315°, such as in the range from 45° to 180°, for example in the range from 45° to 135°. In embodiments, the tertiary angle depends on the number of angular sensing zones on the base plate and/or the sensor patch. For example, the tertiary angle can be about 180°±15°, e.g. for a base plate and/or a sensor patch with three or more sensing zones. The tertiary angle can be about 120°±15°, e.g. for a base plate and/or a sensor patch with three or more sensing zones. The tertiary angle can be about 90°±15°, e.g. for a base plate and/or a sensor patch with three, four or more sensing zones.

Alternatively or additionally, the tertiary sensing zone can be arranged in a tertiary radial space from the centre point of the first adhesive layer. In embodiments, the tertiary radial space spans a tertiary radius in the range from 15-50 mm, such as in the range from 25-50, such as in the range from 29-30 mm. In embodiments, the tertiary radius depends on the number of radial sensing zones on the base plate and/or the sensor patch. In embodiments, the tertiary radius can be greater than the secondary radius and/or the primary radius.

In embodiments, the primary sensing zone and the secondary sensing zone are separate sensing zones, i.e. non-overlapping. The primary sensing zone and the tertiary sensing zone can be separate sensing zones, i.e. non-overlapping. The secondary sensing zone and the tertiary sensing zone can be separate sensing zones, i.e. non-overlapping.

In embodiments, the primary sensing zone, the secondary sensing zone, and/or the tertiary sensing zone cover electrodes embedded in, or in contact with, the first adhesive layer as well as leakage electrodes being exposed to the surroundings. Thereby, the propagation or absorption of moisture in the first adhesive layer can be detected in one or more of the sensing zones, thereby providing for the determination of the direction of moisture propagation in the first adhesive layer. Likewise, output propagating between the skin of the wearer and the first adhesive layer can be determined by the exposed leakage electrodes. The leakage electrodes can be exposed by means of sensor point openings. A sensor point opening of the first adhesive layer is configured to overlap a (sensing) part of a leakage electrode, e.g. to form a sensor point. In embodiments, a sensor point opening of the first adhesive layer has a suitable shape and size facilitating access to a leakage electrode from the proximal side of the first adhesive layer.

In embodiments, two electrodes of the electrode assembly form a sensor. In embodiments, the first leakage electrode and the second leakage electrode form a primary leakage sensor or primary leakage electrode pair for detecting presence of liquid on the proximal side of the first adhesive layer in the primary sensing zone. In embodiments, the second leakage electrode and the third leakage electrode form a secondary leakage sensor or secondary leakage electrode pair for detecting presence of liquid on the proximal side of the first adhesive layer in the secondary sensing zone. In embodiments, the first leakage electrode and the third leakage electrode form a tertiary leakage sensor or tertiary leakage electrode pair for detecting presence of liquid on the proximal side of the first adhesive layer in the tertiary sensing zone.

In embodiments, the base plate and/or the sensor patch comprises a monitor interface (also referred to as an assembly interface). In embodiments, the monitor interface is configured for electrically and/or mechanically connecting the ostomy appliance (base plate and/or sensor patch) to the monitor device. In embodiments, the monitor interface is configured for wirelessly connecting the ostomy appliance (base plate and/or sensor patch) to the monitor device. Thus, the monitor interface of the base plate and/or the sensor patch can be configured to electrically and/or mechanically couple the ostomy appliance and the monitor device.

In embodiments, the monitor interface of the base plate and/or the sensor patch comprises, e.g. as part of a first connector of the monitor interface, a coupling part for forming a mechanical connection, such as a releasable coupling between the monitor device and the base plate and/or the sensor patch. In embodiments, the coupling part is configured to engage with a coupling part of the monitor device for releasably coupling the monitor device to the base plate and/or the sensor patch.

The present disclosure provides a monitor device comprising a three-axis accelerometer configured to generate a position signal. The three-axis accelerometer is configured for assessing/measuring (relative) acceleration, the direction of gravity, and the force of gravity along an x-axis, a y-axis, and a z-axis being mutually orthogonal, i.e. spanning a (three-dimensional) Cartesian coordinate system. In embodiments, the accelerometer is configured to detect movement of the monitor device. A three-axis accelerometer can be denoted a tri-axial accelerometer. In embodiments, the assessed/measured acceleration, direction of gravity, and/or force of gravity is contained in a position signal. Thereby, the monitor device is capable of measuring relative acceleration (movement) and the force of gravity in a three-dimensional space, i.e. the space as spanned by a Cartesian coordinate system. In particular, the monitor device is capable of measuring relative acceleration and the force of gravity along each of the x-axis, y-axis, and z-axis of such a three-dimensional space. In embodiments, the position signal is communicated to the processor and/or a memory of the monitor device. In embodiments, the position signal forms basis for a determination of a spatial orientation, such as a tilt, of the monitor device.

In embodiments, the accelerometer is configured to generate one or more position signals proportional to an acceleration of the monitor device relative to the one or more axes of the three-dimensional coordinate system, which position signals can represent movement of the monitor device (through wearing the monitor device) or user input (through tapping on the monitor device). In embodiments, tapping, or tapping sequences, is a procedure wherein the user uses his/her finger or equivalent to generate certain position signals, such as position signals pertaining to a certain pattern of tapping (task profile). Thus, usually, tapping pertains to short but significant movements of the monitor device. In other words, tapping causes the monitor device to move by a relatively high acceleration due to the short period of time the monitor device is moved during each tap.

In the following, whenever referring to a certain axis, such as an x-axis, a y-axis, or a z-axis, of the accelerometer, the referral is to the axis along which an acceleration can be measured/sensed by such 3-axis accelerometer. In embodiments, the accelerometer measures along all three axes simultaneously. Thus, the referral is to the concept of sensing, measuring, or generating position signals proportional to an acceleration along the certain axis rather than a physical shape of the accelerometer. It shall be understood that a referral to a certain axis, such as the x-axis, can as well be substituted by a referral to any other axis, such as the y-axis and z-axis, by applying a rotation of the reference frame/coordinate system. Rotation of the reference frame/coordinate system can be through appliance of a rotation matrix according to linear algebra. Thus, in embodiments, the referral to a specific axis is merely for illustrative purposes. The same reasoning applies to any referral to a geometric plane spanned by the axes.

In embodiments, the accelerometer comprises certain processing capabilities, such that the accelerometer can be turned on irrespectively of the power status of the processor of the monitor device. For example, the processing capabilities of the accelerometer include analysing the position signals and send relevant instructions to the processor. In embodiments, the accelerometer is capable of turning the processor of the monitor device on/off as part of a power management system.

In embodiments, the accelerometer is a capacitive MEMS accelerometer. In embodiments, the accelerometer is a piezoelectric accelerometer. In embodiments, the accelerometer is a piezoresistive accelerometer. In embodiments, the accelerometer has analog outputs. In embodiments, the accelerometer has digital outputs. In embodiments, the accelerometer is capable of measuring at least +/−2 g. In embodiments, the accelerometer can measure acceleration between −50 g and 50 g, such as between −20 g and 20 g, or such as between −10 g and 10 g. In embodiments, the accelerometer has a bandwidth of at least 10 Hz, such as 50 Hz.

The present disclosure provides for the use of a base plate and/or sensor patch comprising multiple sensing zones, such as angularly distributed sensing zones as previously described. In embodiments, the present disclosure provides for communicating to the user in which zone a leakage is occurring. In embodiments, the user is free to apply the base plate and/or sensor patch at any angle of rotation about his/her ostomy. For example, presence of scars and/or wrinkles in the skin can cause the user to rotate the base plate and/or sensor by a certain angle, e.g. based on personal experience and/or comfort. In embodiments, the base plate and/or sensor patch appears to be rotationally symmetric to the user, despite the sensing zones being provided in a certain array in a sensor assembly of the base plate and/or sensor patch. In one embodiment, the data from the sensing zones are collected by the monitor device through a physical connection to the electrodes of the electrode/sensor assembly. In embodiments, such physical connection is provided by a neck portion attached to/integral with the base plate and/or sensor patch, whereby the electrodes of the electrode assembly can extend into the neck portion and connect with a coupled monitor device in an assembly interface. Thus, in embodiments, the base plate and/or the sensor patch comprises a neck portion extending radially away from the user's stoma, the neck portion comprising an assembly interface allowing a monitor device to be coupled to the base plate and/or sensor patch, and therethrough to the electrode/sensor assembly. In embodiments, the monitor device is configured for being coupled to the base plate and/or sensor patch, and thus to be worn in close proximity to the skin of the user. Thus, the monitor device is configured for being coupled to the base plate and/or sensor patch in a designated portion thereof and remains in such fixed position relative to the base plate and/or sensor patch during use, i.e. during monitoring, such as leakage monitoring, of the base plate and/or sensor patch. By being coupled to the base plate and/or sensor patch in a fixed position, the spatial orientation of the monitor device, such as a tilt relative to a natural orientation, is indicative of an equivalent tilt/rotation of the base plate and/or sensor patch. In other words, the (coupled) monitor device is fixed relative to sensing zones provided in a sensor assembly of the base plate and/or sensor patch. In further other words, the spatial orientation of a monitor device coupled to a base plate and/or sensor patch applies likewise to the base plate and/or sensor patch through their fixed relative position.

By providing the monitor device with an accelerometer, it is possible to determine the spatial orientation of such a monitor device. Thereby, since the monitor device is configured for being coupled to the base plate and/or sensor patch in a fixed position, it is possible to determine the spatial orientation, such as a rotational offset, of the base plate and/or the sensor patch relative to the ostomy, and as such of the sensing zones provided in the base plate and/or sensor patch.

Thereby, it is possible to communicate to the user where (in which sensing zone) a possible leakage is occurring and/or where moisture content absorbed in the adhesive is high/increasing.

In an embodiment, the position signal comprises a value for a force of gravity along the x-axis, along the y-axis, and along the z-axis, the axes being mutually orthogonal, and/or a value for a primary angular offset of the x-axis relative to a predefined orientation, a secondary angular offset of the y-axis relative to a predefined orientation, and a tertiary angular offset of the z-axis relative to a predefined orientation.

In embodiments, the x-axis, the y-axis, and the z-axis are mutually orthogonal in accordance with the Cartesian coordinate system as covered by the 3-axis accelerometer as previously described.

In embodiments, the position signal is mathematically represented as a vector or a matrix. In embodiments, the position signal further comprises a timestamp. By applying trigonometric functions, the total force of gravity can be calculated. In the following, the force of gravity g is measured in Newton ([N]), and for an object in free fall, 1 g=9.8 N=9.8 m/s$^2$.

In embodiments, the position signal comprises information pertaining to the force of gravity along the x-axis, the force of gravity along the y-axis, and the force of gravity along the z-axis.

In embodiments, additionally or alternatively, the position signal comprises information pertaining to a primary angular offset of the x-axis relative to a predefined orientation, a secondary angular offset of the y-axis relative to a predefined orientation, and a tertiary angular offset of the z-axis relative to a predefined orientation.

In embodiments, by an angular offset is meant the angular deviation between a predefined orientation and a given axial component, such as the x-axis, the y-axis, or the z-axis. In embodiments, a predefined orientation is an orientation wherein one of the axes (such as the x-axis, or the y-axis, or the z-axis) is aligned with the direction of gravity, whereas the remaining set of axes (such as the y-axis and the z-axis, or the y-axis and the x-axis, or the z-axis and the x-axis) span a geometric (horizontal) plane being normal/perpendicular to the direction of gravity. For example, an angular offset of an axis can be measured relative to the direction of gravity or relative to the horizontal plane.

In embodiments, the position signal comprises a value for a relative acceleration of the monitor device along the x-axis, the y-axis, and the z-axis. Thereby, information pertaining to a movement of the monitor device can be directly read from the position signal, or from two or more position signals. In embodiments, relative acceleration is indicative of a movement of the monitor device. In embodiments, the relative acceleration can be calculated from the information pertaining to the force of gravity along the x-axis, along the y-axis, and along the z-axis.

In embodiments, the predefined orientation is a predefined natural orientation of the accelerometer. In embodiments, an angular offset denotes deviations from the natural orientation. Thus, in embodiments, an angular offset indicates a tilt of the accelerometer and hence of the monitor device comprising said accelerometer. In embodiments where the monitor device is coupled to a base plate and/or sensor patch comprising a sensor assembly, in particular a sensor assembly comprising two or more sensing zones, indication of a tilt of the monitor device is likewise an indication of a tilt/rotational offset of the base plate and/or sensor patch. In embodiments, the processor generates an offset parameter based on one or more position signals. In embodiments, the offset parameter is used to compensate for a tilt of the monitor device/base plate/sensor patch when communicating the presence and position of a possible leakage relative to the ostomy.

In an embodiment, the position signal is sampled at a rate of at least 0.1 Hz. In other words, in embodiments, the sampling rate of the position signal is at least 0.1 Hz. In further other words, a position signal is obtained at least every tenth second. By sampling the position signal is meant that a position signal is obtained by the accelerometer at least every tenth second. Thereby, every tenth second, the spatial orientation of the accelerometer, and hence the monitor device, is assessed. In embodiments, the position signal is sampled at a rate of at least 1 Hz, i.e. once every second. In embodiments, the sampling rate is at least 100 Hz, or at least 200 Hz, or at least 2000 Hz. By increasing the sampling rate, a more accurate assessment of the spatial orientation of the monitor device is obtained. In embodiments, such more accurate assessment is useful for a registration of tapping sequences as previously described. In addition, such more accurate assessment provides for the possibility of using the monitor device to track activity and/or physiological changes such as steps taken by the user, time spent in bed, breathing rhythm, or heartbeat.

In embodiments, the monitor device is capable of activity tracking the user wearing the monitor device, i.e. to monitor movements and, possibly, the intensity of such movements. In other words, in embodiments, the monitor device tracks the activity of the user through the generation of position signals pertaining to movement of the monitor device, and hence of the user. In embodiments, during activity tracking, the sample rate is at least 100 Hz, or at least 200 Hz, or at least 2000 Hz. In embodiments, the monitor device is capable of differentiating different activities, including walking, running, cycling, tennis etc. In embodiments, such different activities yield different movements and hence different (distinguishable) position signals, which can be assigned the different activities. In embodiments, data pertaining to activity tracking can be communicated to a system capable of determining or predicting a future operating state of the ostomy appliance. In other words, in embodiments, a system is capable of determining or predicting the possibility of a leakage or deterioration of the adhesive properties of the ostomy appliance. In embodiments, such system is capable of warning the user (e.g. through an accessory device) of the possibility of a leakage, e.g. due to a certain activity as tracked and determined by the monitor device. In embodiments, the data pertaining to activity tracking, e.g. the determined type of activity, is used to predict a generated amount of sweat. In embodiments, a predicted amount of sweat is used to determine a future operating state of the ostomy appliance.

In embodiments, the sampling rate is adjustable, e.g. in accordance with a power management system of the monitor device. In embodiments, the sampling rate depends on a power management mode of the monitor device. In embodiments, the sampling rate is low, such as less than 1 Hz, such as 0.1 Hz, when the monitor device determines that the user is at rest, e.g. during night-time or when he/she is sitting or lying down. In embodiments, the sampling rate is high, such as more than 1 Hz, or more than 100 Hz, such as 2000 Hz, when the monitor device determines that the user is active, such as during daytime or when he/she is walking/exercising.

In embodiments, the monitor device comprises a power management mode wherein the monitor device, or at least the processor, remains in a power save mode (e.g. where the processor is turned off or remains in a sleep mode where certain functionalities are turned off) unless significant accelerations are measured/detected by the accelerometer. In embodiments, significant accelerations are accelerations pertaining to intentional tapping on the monitor device. By significant accelerations are meant accelerations of more than +/−0.2 g, such as more than +/−0.5 g, or such as more than +/−1 g, such as +/−2 g. Thus, a significant acceleration can be defined as a threshold value, e.g. a threshold value incorporating one of the exemplary accelerations. Thereby, battery is saved as long as the monitor device is only exposed to minor accelerations, i.e. accelerations being less than a threshold value defining a significant acceleration as explained above. Thus, in embodiments of the power management mode, the accelerometer does not respond to minor accelerations, but is configured to respond to significant accelerations as defined above. Thus, in embodiments, once exposed to significant accelerations, the accelerometer instructs the processor to exit the power save mode.

In an embodiment, the position signal is indicative of a spatial orientation of the monitor device. In embodiments, the position signal is indicative of a spatial orientation of the monitor device relative to the predefined natural orientation. Since the position signal comprises information pertaining to a relative acceleration, the force of gravity, and/or an angular offset/tilt, and since the accelerometer is fixed inside the monitor device, the spatial orientation of the monitor device can be determined. In embodiments, a movement of the monitor device is determined by calculating a difference between two position signals separated in time. Thereby, (relative) movements of the monitor device can be tracked. In embodiments where the monitor device is coupled to a base plate and/or sensor patch comprising a sensor assembly, in particular a sensor assembly comprising two or more sensing zones, indication of a tilt of the monitor device is likewise an indication of a tilt/rotational offset of the base plate and/or sensor patch. Thereby, the position signal can be used to generate an offset parameter used to compensate for such a tilt when communicating the presence and position of a possible leakage relative to the ostomy to the user, e.g. through a graphical user interface (GUI), such as a GUI included in an accessory device, such as a smartphone.

In an embodiment, the accelerometer comprises a predefined natural orientation wherein the primary angular offset of the x-axis relative to the direction of gravity is zero, or the secondary angular offset of the y-axis relative to the direction of gravity is zero, or the tertiary angular offset of the z-axis relative to the direction of gravity is zero.

By introducing/defining a natural orientation, such natural orientation forms a reference for any tilt/rotation offset. In embodiments, the natural orientation is an orientation of the accelerometer, and hence of the monitor device, wherein one of the axes (x, y, z) of a Cartesian coordinate system are aligned with the direction of gravity, and wherein the remaining set of axes span a geometric (horizontal) plane being perpendicular/normal to the direction of gravity. In embodiments, the natural orientation is defined as the situation wherein the y-axis is aligned with the direction of gravity and the x-axis and the z-axis span a geometric plane thereby being horizontal. In embodiments, the natural orientation is defined as the situation wherein the x-axis is aligned with the direction of gravity, and the y-axis and the z-axis span a geometric plane thereby being horizontal. In embodiments, the natural orientation is defined as the situation wherein the z-axis is aligned with the direction of gravity, and the x-axis and the y-axis span a geometric plane thereby being horizontal. In embodiments, by being aligned is meant that the respective axis is parallel with the direction of gravity, but that the direction of the axis can be either positive or negative in the direction of gravity. In embodiments, the natural orientation is predefined by the manufacturer, thereby allowing the manufacturer or a service provider to know how to communicate the leakage state (where a leakage is occurring). In embodiments, the natural orientation is resettable or redefinable, such as by the user.

Using other words, a natural orientation can be denoted a neutral orientation or a default orientation.

In an embodiment, the accelerometer comprises a predefined natural orientation wherein the force of gravity along the x-axis of the accelerometer is 0 g, and wherein the force of gravity along the y-axis of the accelerometer is −1 g.

Thereby is provided a specific embodiment of a natural orientation wherein the y-axis of the accelerometer is parallel with the direction of gravity, and wherein the positive direction of the y-axis is opposite the direction of gravity, i.e. the force of gravity along the y-axis is −1 g. Likewise, since the x-axis is orthogonal the y-axis according to a Cartesian coordinate system, the force of gravity along such x-axis is 0 g. Consequently, the force of gravity along the z-axis is likewise 0 g. In embodiments, the force of gravity along the y-axis is +1 g. Thus, according to the embodiment, the x-axis and z-axis span a geometric plane being horizontal, i.e. perpendicular to the direction of gravity and the y-axis. Thus, the direction of gravity is normal to the geometric plane spanned by the x-axis and the z-axis.

In embodiments, the accelerometer comprises a predefined natural orientation wherein the force of gravity along the y-axis is +/−1 g. In embodiments, the accelerometer comprises a predefined natural orientation wherein the force of gravity along the x-axis is +/−1 g. In embodiments, the accelerometer comprises predefined natural orientation wherein the force of gravity along the z-axis is +/−1 g.

In an embodiment, the accelerometer is configured to determine its spatial orientation relative to an ostomy of a user based on a pattern of movement generated by the user.

In embodiments, the pattern of movement is generated by a user wearing the monitor device. When the user has attached the base plate and/or sensor patch to the peristomal skin area, i.e. the sensor assembly at least partly surrounds an ostomy, it is a challenge to know how possible sensing zones of the sensor assembly are arranged relative to the ostomy. For most users, it will be natural to consider "up" as the direction pointing towards the head and "down" as the direction pointing towards the lower body/feet. However, such terminology can be considered vague in a general sense when the user is exercising, lying down, sitting, standing on his/her head, etc. Thus, a monitor device capable of determining its, and as such the sensor assembly's, spatial orientation relative to an ostomy is desired. As previously disclosed, in embodiments, by knowing the spatial orientation of the monitor device, any rotation of the sensor assembly (potentially comprising sensing zones) can be deduced.

In embodiments, the accelerometer is configured to generate position signals at a certain sampling rate, such as 0.1 Hz or 1 Hz, or more than 1 Hz, such as when the monitor device is coupled to the base plate and/or sensor patch, and the base plate and/or sensor patch is attached to the peristomal skin area, i.e. the sensor assembly of the base plate and/or sensor patch surrounds the ostomy. Each position signal comprises information pertaining to the spatial orientation of the monitor device at the time a specific position signal was generated. Thus, in embodiments, by sampling over a certain time interval, a trend in the position signals is formed. For example, if the user, after attachment of the base plate and/or sensor patch and the monitor device, walks around/stands up, the trend can reveal an average angular offset of the monitor device relative to a predefined natural orientation. In embodiments, the average angular offset is indicative of the rotational offset of the sensor assembly of the base plate and/or sensor patch relative to the natural orientation. In embodiments, the pattern of movement/the position signals generated by a standing/walking user is different from a bedbound user and from a sitting user. Thereby, in embodiments, the monitor device is configured to differentiate different body positions.

In embodiments, the average angular offset is communicated to an accessory device, such as a smartphone. In embodiments, the accessory device comprises a GUI configured for displaying a visual representation of the at least two sensing zones of the sensor assembly. In embodiments, the visual representation comprises information pertaining to a state of the region covered by the respective sensing zone, where the state can be an indication of a presence of liquid, e.g. a leakage. In embodiments, the average angular offset is applied to the visual representation, e.g. to a mathematical model generating the visual representation, in a way to reflect the physical orientation of the sensor assembly in the visual representation relative to the user's ostomy. For example, if the user prefers to wear his/her base plate and/or sensor patch slightly rotated due to the presence of scars or wrinkles, such rotation is reflected in the visual representation in the GUI. In particular, the presence of a neck portion being integral with the base plate and/or sensor patch can cause the user to rotate his/her base plate and/or sensor patch to avoid attaching an adhesive surface of such a neck portion to scars and/or wrinkles.

In an embodiment, the pattern of movement comprises a plurality of position signals sampled during a predefined amount of time. In embodiments, the predefined amount of time depends on the sampling rate of the plurality of position signals. In embodiments, the predefined amount of time is between 1 minute and 60 minutes, such as between 1 minute and 30 minutes, such as between 5 minutes and 20 minutes, such as 10 minutes. In embodiments, the pattern of movement is generated continuously from the movement of the user. In embodiments, the pattern of movement comprises a plurality of position signals sampled during a floating amount of time, such as the preceding 10 minutes, or any preceding amount of time selected between 1 minute and 60 minutes, such as the preceding 30 minutes.

In embodiments, the average angular offset is based on a calculated mean/average of at least 10 position signals, or at least 100 position signals, or at least 500 position signals. In embodiments, the average angular offset is indicative of the rotational offset of the base plate and/or sensor patch relative to a predefined natural orientation.

In an embodiment, the spatial orientation of the accelerometer is indicative of a rotational offset of the sensor assembly when the monitor device is coupled to said sensor assembly. In embodiments, the monitor device is coupled to a sensor assembly of a base plate or a sensor patch. Thereby, the spatial orientation, such as a tilt, of the accelerometer, and thereby of the monitor device, is indicative of/corresponds to a rotational offset of the sensor assembly. In embodiments, the rotational offset is relative to a natural orientation, such as a natural orientation as previously disclosed. In embodiments, the spatial orientation of the accelerometer is indicative of the position of one or more, such as two or more, sensing zones relative to an ostomy. In embodiments, the spatial orientation of the accelerometer is an average angular offset of the accelerometer, and as such an averaged value obtained from a plurality of position signals as described above.

In an embodiment, the processor is configured to generate an offset parameter based on an angular offset of the accelerometer from its natural orientation. In an embodiment, the processor is configured to communicate the position signal and/or the offset parameter to an accessory device.

In embodiments, the accelerometer is configured to generate an offset parameter based on an angular offset of the accelerometer from its natural orientation. In embodiments, the monitor device is coupled to a sensor assembly of a base plate or a sensor patch. Thus, in embodiments, the offset parameter is a parameter indicative of a rotational offset of the sensor assembly relative to a natural orientation. In embodiments, the angular offset can be considered pertaining to a two-dimensional plane, such as a geometric plane spanned by two of the axes of the accelerometer, the geometric plane being selected such as to be substantially parallel with a plane in which the base plate and/or sensor patch resides.

In embodiments, the offset parameter is communicated to an accessory device. In embodiments, the monitor device comprises a transceiver for wirelessly communicating with an accessory device. In embodiments, the monitor device is configured to transmit a signal indicative of the offset parameter to an accessory device. In embodiments, by communicate, e.g. to communicate a parameter from the monitor device to an accessory device, is meant to transmit a signal indicative of the parameter, such as according to a wireless protocol, such as through a Bluetooth connection. In embodiments, the accessory device comprises a graphical user interface. In embodiments, the offset parameter is used to generate a visual representation of the sensor assembly, such that the visual representation incorporates the rotational offset of the physical sensor assembly as applied to the peristomal skin area via the base plate or the sensor patch.

In an embodiment, the housing comprises a skin facing surface, and the x-axis and the y-axis of the accelerometer span a geometric plane being substantially parallel with said skin facing surface of the housing, and the z-axis of the accelerometer extends in a direction being normal to said geometric plane. In embodiments, the housing defines the spatial extension of the monitor device, i.e. the outer shape of the monitor device. In embodiments, the monitor device, and as such the housing thereof, is configured for being worn by a user underneath his/her clothing, near an ostomy, such that the monitor device can obtain data related to a sensor assembly arranged in the peristomal skin area. Thus, in embodiments the housing is small and/or discreet. In embodiments, the housing comprises a skin facing surface being substantially planar to flush with the skin or a neck portion of the base plate and/or sensor patch. In embodiments, the substantially planar skin facing surface is parallel with the geometric plane spanned by the x-axis and the y-axis of the accelerometer, whereby the z-axis of the accelerometer is normal to the geometric plane. In embodiments, the substantially planar skin facing surface of the housing is adapted to be arranged in parallel with a geometric plane spanned by the base plate and/or sensor patch. Thereby, consequently, the geometric plane spanned by the x-axis and y-axis of the accelerometer is adapted to be arranged in parallel with the geometric plane spanned by the base plate and/or sensor patch.

Thereby, the accelerometer and the housing share a certain geometry useful for giving the user a sense of orientation of the monitor device. Moreover, a tilt of the accelerometer in the geometric plane spanned by its x- and y-axis corresponds to a tilt of the base plate and/or sensor patch, since the geometric plane spanned by the base plate and/or sensor patch is parallel with the geometric plane spanned by the x- and y-axis of the accelerometer, and since the accelerometer (as fixed in the housing of the monitor device) is fixed relative to the base plate and/or sensor patch.

In embodiments, the x-axis and the z-axis of the accelerometer span a geometric plane being substantially parallel with the skin facing surface of the housing, and the y-axis of the accelerometer extends in a direction being normal to said geometric plane.

In embodiments, the y-axis and the z-axis of the accelerometer span a geometric plane being substantially parallel with the skin facing surface of the housing, and the x-axis of the accelerometer extends in a direction being normal to said geometric plane.

In embodiments, two axes selected from the x-axis, the y-axis, and the z-axis of the accelerometer span a geometric plane being substantially parallel with the skin facing surface of the housing, and the axis of the accelerometer not selected extends in a direction being normal to said geometric plane.

In an embodiment, the appliance interface is configured for coupling to a plurality of electrodes forming at least two sensors arranged in at least two separate sensing zones configured for monitoring a peristomal skin surface. In embodiments, by monitoring is meant that the sensors are configured for detecting presence of liquids, such as output, in the peristomal skin are, or (an increase of) moisture content in the adhesive layer of the base plate and/or sensor patch. In embodiments, the appliance interface comprises the number of terminals required to connect to a corresponding number of electrodes. In embodiments, two electrodes form a sensor. In embodiments, two sensors require the presence of four electrodes. In embodiments, the first and the second electrode share a common ground and as such, three electrodes is sufficient for forming two sensors. Thus, in embodiments where one of the electrodes is a common ground, the appliance interface comprises at least three terminals configured for coupling with three electrodes. The at least two sensors are arranged in at least two sensing zones. The sensing zones can be a primary and a secondary sensing zone arranged in a primary and a secondary angle space about an ostomy.

In an embodiment, the processor is configured for determining a spatial distribution of the at least two sensing zones based on one or more position signals. In embodiments, the processor is configured for determining a spatial distribution of the at least two sensors based on one or more position signals, such as relative to an ostomy when the monitor device is attached a base plate or a sensor patch adhered to the peristomal skin surface. As previously disclosed, by knowing an angular offset of the monitor device relative to a natural orientation, and as such of the sensor assembly when the monitor device is coupled to the sensor assembly, it is possible to determine how the at least two sensing zones are distributed about an ostomy. In particular, by knowing how the sensor assembly as a whole is rotated about an ostomy relative to a natural orientation, and by knowing how the sensor zones are arranged in the sensor assembly, is it possible to determine the actual spatial distribution as applied to the peristomal skin. In embodiments, the arrangement of the sensing zones in the sensor assembly is predefined. In embodiments, the arrangement of the sensing zones in the sensor assembly is predefined by a manufacturer.

In an embodiment, one or more task profiles are stored on a memory of the monitor device, and to the monitor device is configured to detect one or more tapping sequences contained in one or more position signals. In embodiments, the memory is a non-transitory memory. The one or more task profiles may correspond to one or more tapping sequences generated by a user and contained in one or more position signals. By a tapping sequence being contained in one or more position signals is meant that the position signals comprise information pertaining to any movements of the monitor device (accelerometer), such as taps as applied by a user. As such, movements of the monitor device (accelerometer) due to such tapping is contained in one or more position signals. In embodiments, the sample rate of position signals is at least 1 Hz, or at least 10 Hz, or at least 2000 Hz in order to resolve a tapping sequence.

For example, a tapping sequence can be two short and substantially identical taps on the monitor device by a finger. Such a tapping sequence can be compared to a certain task profile stored on a memory of the monitor device, i.e. a certain task profile may correspond to two short and substantially identical taps on the monitor device by a finger. By comparing a detected tapping sequence (i.e. by comparing one or more position signals) with the one or more task profiles stored on a memory of the monitor device, it is possible to assign an output/action to each of the tapping sequences. Thereby, in embodiments, the user can control certain aspects of the monitor device simply by tapping on the monitor device.

In an embodiment, the processor is configured to compare a given tapping sequence of the one or more tapping sequences with the one or more task profiles and generate an output associated with the given tapping sequence. In embodiments, the output is configured for affecting a functionality of the monitor device. By an output is meant an action affecting the functionality of the monitor device. In embodiments, when tapping on the monitor device, the caused movements are detected by the accelerometer and contained in one or more the position signals. In embodiments, the position signals, i.e. the tapping sequence, are compared with one or more task profiles. In embodiments, the comparison is made by the processor. In embodiments, the comparison is made by the accelerometer. In embodiments, a certain output is generated based on a finding of compliance between a stored task profile and the detected tapping sequence. In embodiments, the output, and thereby the subsequently caused functionality of the monitor device, depends on the specific tapping sequence.

In an embodiment, the output is selected from waking up the monitor device from a sleep mode, activating pairing mode, or to enter sleep mode. In embodiments, the output depends on the given tapping sequence. In embodiments, the output affects the functionality of the monitor device, e.g. by means of sending appropriate instructions to the processor, the accelerometer, or other components included in the monitor device. In embodiments, functionalities of the monitor device include exiting/entering sleep mode and activating pairing mode. In embodiments, a task profile, when effectuated through the generation of an output, prompting a wake up of the monitor device from a sleep mode is stored in a memory of the monitor device. Thus, in embodiments, by tapping on the monitor device in a first certain pattern/by a certain first tapping sequence, the monitor device wakes up from a sleep mode. In embodiments, by a tapping on the monitor device in a second certain pattern/ by a certain second tapping sequence, the monitor device enters/activate pairing mode. In embodiments, a pairing mode is a mode of the monitor device wherein a transceiver included in the monitor device is active for wireless pairing with an accessory device comprising another transceiver. Thereby, by tapping by a certain second pattern, the user can connect the monitor device to an accessory device through a wireless connection. In embodiments, by a tapping on the monitor device in a third certain pattern/by a certain third tapping sequence, the monitor device enters sleep mode. In embodiments, a sleep mode is a state wherein the monitor device saves battery/power by turning certain, preselected, functionalities off.

In embodiments, in response to a certain tapping sequence, the monitor device can enter a flight mode, wherein wireless connections are turned off. Thus, by tapping on the monitor device according to a certain task profile, the wireless connections can be turned off, e.g. to comply with regulations pertaining to such wireless connections. In embodiments, the monitor device can exit flight mode by tapping on the monitor device according to a second task profile. In embodiments, functionalities of the monitor device include entering/exiting flight mode.

In embodiments, obtaining ostomy data, as previously described, is a default functionality of the monitor device automatically activated through coupling the monitor device to a sensor assembly. In embodiments, obtaining ostomy data is a functionality of the monitor device controllable through a tapping sequence.

Thereby, the user can control different functionalities of the monitor device merely by tapping anywhere on the monitor device, the tapping resulting in a movement of the monitor device, and as such in a position signal generated by the accelerometer comprising information pertaining to/indicative of the movement.

In an embodiment, the monitor device is configured for turning off or entering a sleep mode if no movement has been detected for a predetermined amount of time. In embodiments, if a plurality of consecutive position signals is identical, the monitor device is configured to turn off or enter a sleep mode. In embodiments, if, within a certain time period, such as 10 minutes, obtained position signals are identical, the monitor device is configured to turn off or enter a sleep mode. In practice, it is generally impossible for a living human to wear a monitor device comprising an accelerometer for a prolonged time (e.g. 10 minutes) without causing a detectable movement, i.e. without the movement is detected/sensed by the accelerometer and the information pertaining to the movement is contained in a position signal. Thus, in embodiments, if a plurality of position signals is identical (or; if the plurality of consecutive position signals being sampled in the predetermined amount of time is identical), it is indicative of a non-worn monitor device. In embodiments, the number of consecutive position signals to be identical before the monitor device is turned off or enters sleep mode (i.e. the predetermined amount of time) can be specified by the user or the manufacturer. In embodiments, the number of consecutive position signals to be identical before the monitor device is turned off or enters sleep mode depends on the sampling rate, such that the monitor device can be turned off after 1 minute, irrespective of the sampling rate. In other words, for sampling rate of 0.1 Hz, six position signals are generated within a minute, whereas for a sampling rate of 1 Hz, 60 position signals are generated within a minute. Thus, in embodiments, the monitor device is turned off depending on an elapsed time comprising identical position signals. In embodiments, the monitor device is turned off or enters sleep mode if no movement has been detected (i.e., identical position signals) for at least 1 minute, such as for 1 minute, or such as for 5 minutes, or such as for 10 minutes.

In embodiments, the monitor device stays turned off or sleeps until, for example, the user manually turns the monitor device back on. In embodiments, when the monitor device is turned off or sleeps, the accelerometer can periodically wake up and check for movement. Thereby, in embodiments, when the accelerometer senses movement, e.g. through generating two non-identical position signals, the monitor device can be turned back on automatically.

According to a second aspect of the invention, a method for determining a rotational offset of a sensor assembly of an ostomy appliance relative to an ostomy is disclosed. The sensor assembly is couplable to a monitor device, such that the position of the monitor device relative to the sensor assembly is fixed. The monitor device comprises a housing, a processor arranged in the housing, and an appliance interface configured for coupling the monitor device to the sensor assembly, the appliance interface comprising a plurality of terminals for connecting with a plurality of electrodes of the sensor assembly. Further, the monitor device comprises a (3-axis) accelerometer configured to generate a position signal. The sensor assembly comprises a plurality of electrodes forming two or more sensors, such as two or more sensors being configured for determining a presence of liquid in a peristomal skin area. The two or more sensors are arranged in at least two separate sensing zones, such as for monitoring the peristomal skin area. Further, the sensor assembly comprises an assembly interface configured for coupling with the appliance interface of the monitor device. The method comprises the steps of obtaining one or more position signals from the accelerometer (e.g., when the ostomy appliance comprising the sensor assembly has been arranged in a peristomal skin area and the monitor device is coupled to the sensor assembly) and determining a rotational offset of the sensor assembly based on the one or more position signals. The rotational offset may be relative to a natural orientation of the accelerometer. The one or more position signals are indicative of (i.e., comprises information pertaining to) a spatial orientation of the accelerometer, and thus of the monitor device as such.

In embodiments, the ostomy appliance is a base plate and/or sensor patch as previously described. Thus, the ostomy appliance is provided with an adhesive, such as a first adhesive layer, such as to provide attachment to the peristomal skin area.

Thereby is provided a method for determining the rotational offset of a sensor assembly relative to an ostomy, in particular where the rotational offset is determined relative to a predefined natural orientation. The method utilizes a monitor device as previously disclosed in relation to the first aspect of the invention. As such, the above disclosed embodiments of the monitor device apply likewise to a monitor device for use in a method for determining a rotational offset of a sensor assembly relative to an ostomy as disclosed herein.

In an embodiment, the method comprises an initial step of defining a natural orientation of the monitor device/accelerometer of the monitor device. In embodiments, the natural orientation is defined according to the above-disclosed embodiments pertaining to the monitor device. In embodiments, the natural orientation of the monitor device is defined by the user, e.g. through arranging the monitor device on a plane/horizontal surface according to a predefined procedure. In embodiments, the natural orientation of the monitor device is predefined by the manufacturer.

In an embodiment, the monitor interface is in communication with an accessory device comprising a graphical user interface, and the method further comprises the steps of communicating the rotational offset to the accessory device and generating (e.g., by means of a processor of the accessory device) a visual representation in the graphical user interface. The visual representation incorporates the rotational offset and illustrates the position of the at least two sensing zones relative to an ostomy. In embodiments, the accessory device (also referred to as an external device) is a mobile phone, such as a smartphone, or another handheld device. In embodiments, the accessory device is a personal electronic device, e.g. a wearable, such as a watch or other wrist-worn electronic device. In embodiments, the accessory device is a docking station. In embodiments, the docking station is configured to electrically and/or mechanically couple the monitor device to the docking station.

In embodiments, the graphical user interface (GUI) is a screen configured for displaying the visual representation of the at least two sensing zones relative to an ostomy. In embodiments, the visual representation is included in an application (app) of the accessory device. In embodiments, the visual representation visualizes the position of the at least two sensing zones relative to an ostomy about which a sensor assembly included in a base plate and/or sensor patch is arranged. Thereby, the visual representation provides an easily accessible way of communicating to the user the state of his/her base plate and/or sensor patch, e.g. in a way of communicating the possible presence of a leakage, i.e. the presence of a liquid, such as output, in the peristomal skin area. By the visual representation incorporating the rotational offset is meant that the rotational offset is implemented in the visual representation, such that the visual representation visualizes the sensor assembly including any possible rotational offset. Thereby, the user is provided with an easy-to-understand visualization of his/her base plate and/or sensor patch comprising a sensor patch, and he/she can better see and comprehend where (in which sensing zone) a possible leakage is occurring, or where (in which sensing zones) the adhesive is weakening due to an increased/large moisture absorption in an adhesive layer.

In embodiments, a plurality of sensing zones is provided, each sensing zone spanning a (separate) angle space. In embodiments, the rotational offset is used as a correction factor, such that the visualization of the sensor assembly/sensing zones are corrected by the rotational offset. In embodiments, the positions of each of the sensing zones are floating, meaning that the positions of each of the sensing zones are defined by a mathematical model using the rotational offset as an input parameter. For example, the visual representation is static (always looks the same on the screen, as opposed to the above described example where the visual representation reflects the physically adhered base plate and/or sensor patch), but the data used to illustrate a possible leakage is corrected by the rotational offset, such that the visual representation illustrates the leakage as occurring in a position relative to, for example, the neck portion and/or monitor device of the base plate and/or sensor patch, rather than relative to, for example, body features ("up", "down") of the user. In this embodiment, a large plurality of sensing zones (e.g., three or more, such as four or five) enhances the visualization, as more sensing zones provides a better sensitivity.

In a third aspect of the invention, an ostomy system comprising a sensor assembly and a monitor device is provided. The monitor device comprises a housing, a processor arranged in the housing, an appliance interface comprising a plurality of terminals for connecting with a plurality of electrodes of the sensor assembly, and a (e.g., three-axis) accelerometer configured to generate a position signal. The sensor assembly comprises a plurality of electrodes forming two or more sensors, such as being configured for determining a presence of liquid/moisture in a peristomal skin area. The two or more sensors are arranged in at least two separate sensing zones. Further, the sensor assembly comprises an assembly interface configured for coupling with the appliance interface of the monitor device. The monitor device is configured for coupling with the sensor assembly. The monitor device may thereby be fixated relative to the sensor assembly, such that a spatial orientation of the monitor device translates to a corresponding orientation if the sensor assembly. Thereby is provided an ostomy system utilizing a monitor device as disclosed above, the ostomy system being capable of determining a rotational offset of the sensor assembly by means of the provision of a (three-axis) accelerometer in the monitor device.

In an embodiment, the appliance interface is configured for coupling with the assembly interface. In embodiments, the coupling is a mechanical coupling. In embodiments, the coupling is a wireless coupling. In embodiments of a wireless coupling, the monitor device is configured for being attached to the user or an ostomy appliance of the sensor assembly in a predefined and fixed position relative to the sensor assembly.

In an embodiment, the sensor assembly is provided in an ostomy appliance. In embodiments, the ostomy appliance is a base plate or a sensor patch a previously disclosed. Thereby is provided a means for attaching, e.g. adhering, the sensor assembly to the peristomal skin area of the user.

In an embodiment, the accelerometer of the monitor device comprises a predefined natural orientation, and the monitor device is configured for determining a rotational offset of the sensor assembly relative to the predefined natural orientation.

Thereby is provided an ostomy system being capable of determining a rotational offset of the sensor assembly and hence for locating two or more sensing zones provided in the sensor assembly.

DETAILED DESCRIPTION OF THE DRAWINGS

FIG. 1 illustrates an exemplary ostomy system. The ostomy system 1 comprises an ostomy appliance 2 including a base plate 4. The base plate 4 is adapted to support an ostomy pouch (not shown). Further, the ostomy system 1 comprises a monitor device 6 and an accessory device 8 (mobile telephone/smartphone). The monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, e.g. via network 12. The server device 10 can be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data. Based on the processed ostomy data, the monitor device 6 may determine what monitor data that are transmitted to the accessory device 8. In the illustrated ostomy system, the accessory device 8 is a mobile phone, however the accessory device 8 can be embodied as another handheld device, such as a tablet device, or a wearable, such as a watch or other wrist-worn electronic device. Accordingly, the monitor device 6 is configured to determine and transmit monitor data to the accessory device 8. The base plate 4 comprises a coupling member 14 in the form of a coupling ring 16 for coupling an ostomy pouch (not shown) to the base plate (two-part ostomy appliance). The base plate 4 has a stomal opening 18 with a centre point 19. The size and/or shape of the stomal opening 18 is typically adjusted by the user or nurse before application of the ostomy appliance to accommodate the user's stoma.

The ostomy system 1 optionally comprises a docking station 20 forming an alternative/additional accessory device of the ostomy system 1. The docking station 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes.

Figure 2:
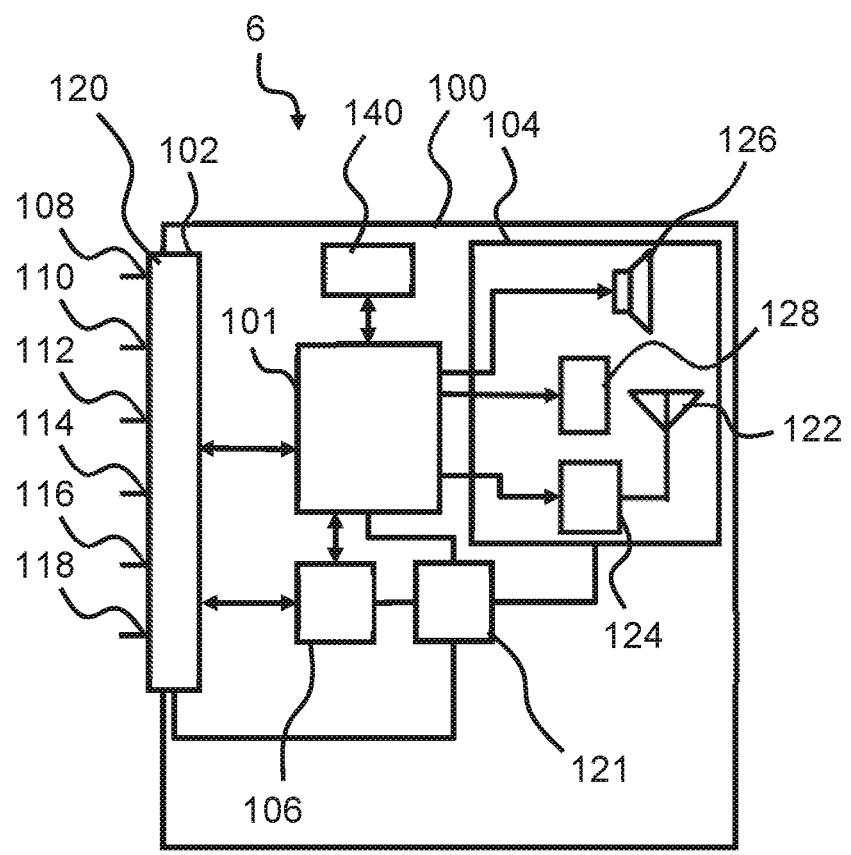
FIG. 2 illustrates an exemplary monitor device of the ostomy system.

FIG. 2 is a schematic block diagram of an exemplary monitor device. The monitor device 6 comprises a monitor device housing 100, a processor 101, and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, e.g. ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory 106. The power unit comprises a battery and charging circuitry. The charging circuitry is connected to the battery and terminals of the first interface 102 for charging the battery via terminals of the first interface, e.g. terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 comprises a 3-axis accelerometer 540 connected to the processor 101.

The processor 101 is configured to apply a processing scheme, and the first interface 102 (appliance interface) is configured for collecting ostomy data from the base plate and/or the sensor patch coupled to the first interface, the ostomy data comprising leakage ostomy data from leakage electrodes of the ostomy appliance. The ostomy data optionally comprises first ostomy data from a first electrode pair of the base plate and/or the sensor patch, second ostomy data from a second electrode pair of the base plate and/or the sensor patch, and/or third ostomy data from a third electrode pair of the base plate and/or the sensor patch. The ostomy data can be stored in the memory 106 and/or processed in the processor 101 in order to obtain parameter data. The parameter data can be stored in the memory 106. The processor 101 is configured to apply a processing scheme, wherein to apply a processing scheme comprises obtaining primary leakage parameter data based on primary leakage ostomy data; obtaining secondary leakage parameter data based on secondary leakage ostomy data; and obtaining tertiary leakage parameter data based on tertiary leakage ostomy data. Optionally the processing scheme comprises obtaining first parameter data based on the first ostomy data; obtaining second parameter data based on the second ostomy data; obtaining third parameter data based on the third ostomy data. In other words, the processor 101 can be configured to obtain first, second and third parameter data based on respective first, second and third ostomy data. To apply a processing scheme comprises to determine an operating state of the base plate and/or the sensor patch of the ostomy appliance based on one or more, e.g. all, of primary leakage parameter data, secondary leakage parameter data, and tertiary leakage parameter data, wherein the operating state is indicative an acute leakage risk in a sensing zone for the ostomy appliance. The monitor device 6 is configured to, in accordance with a determination that the operating state is a primary leakage operating state, transmit a primary leakage monitor signal comprising monitor data indicative of the primary leakage operating state of the base plate and/or the sensor patch via the second interface; and in accordance with a determination that the operating state is a secondary leakage operating state, transmit a secondary leakage monitor signal comprising monitor data indicative of the secondary leakage operating state of the base plate and/or the sensor patch via the second interface. The monitor device 6 can be configured to, in accordance with a determination that the operating state is a tertiary leakage operating state, transmit a tertiary leakage monitor signal comprising monitor data indicative of the tertiary leakage operating state of the base plate and/or the sensor patch via the second interface.

Figure 3:
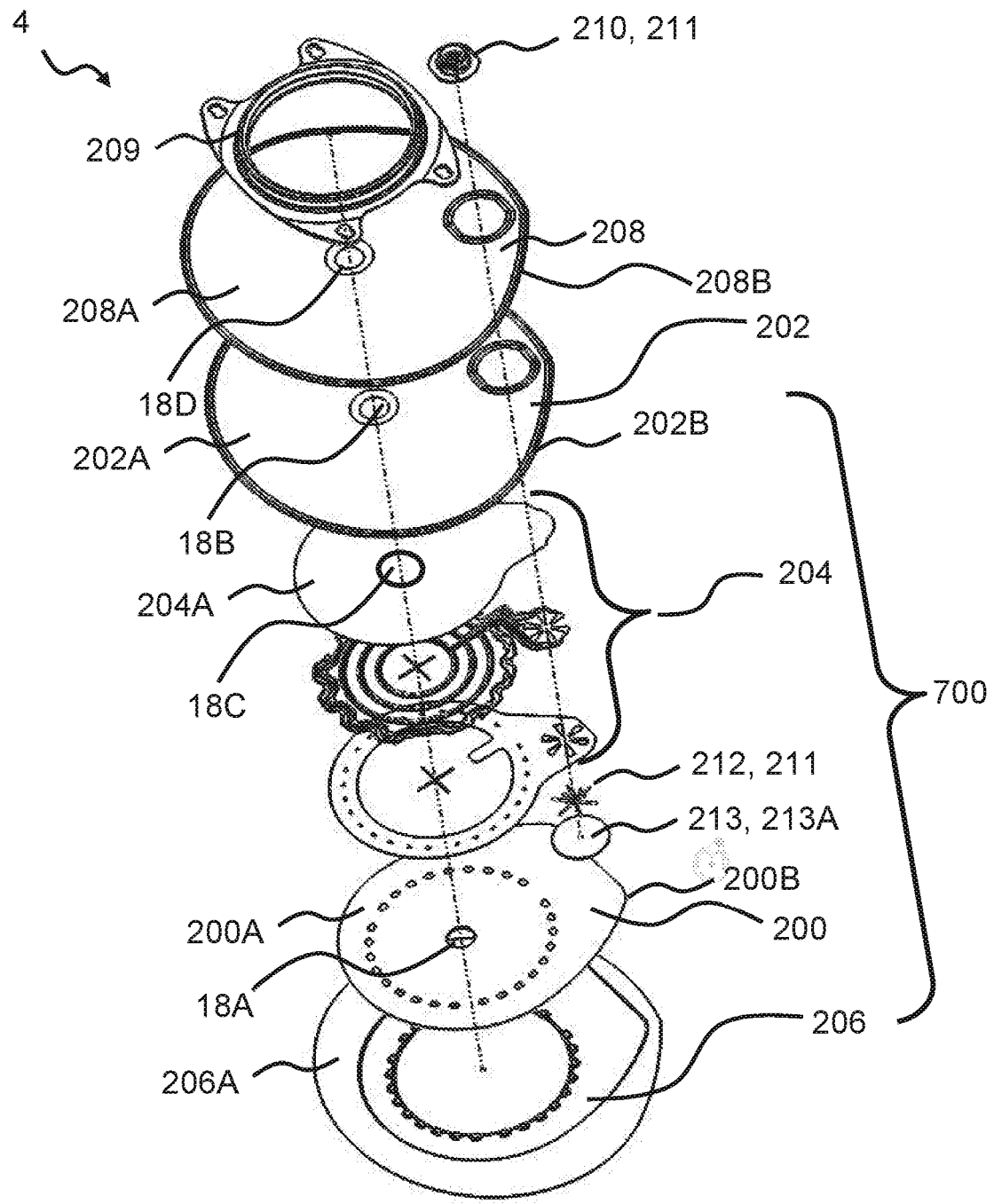
FIG. 3 illustrates an exploded view of a base plate of an ostomy appliance.

FIG. 3 illustrates an exploded view of an exemplary base plate of an ostomy appliance. The base plate 4 comprises a first adhesive layer 200 with a stomal opening 18A. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202, also denoted rim adhesive layer, with a stomal opening 18B. The base plate 4 comprises a plurality of electrodes arranged in an electrode assembly 204. The electrode assembly 204 is arranged between the first adhesive layer 200 and the second adhesive layer 202. The electrode assembly 204 comprises a support layer with stomal opening 18C and electrodes formed on a proximal surface of the support layer. The base plate 4 comprises a release liner 206 that is peeled off by the user prior to applying the base plate 4 on the skin. The base plate 4 comprises a top layer 208 with a stomal opening 18D and a coupling ring 209 for coupling an ostomy pouch to the base plate 4. The top layer 208 is a protective layer protecting the second adhesive layer 202 from external strains and stress during use.

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such as a releasable coupling between the monitor device and the base plate. The coupling part 210 is configured to engage with a coupling part of the monitor device for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the proximal side of the electrode assembly. The first intermediate element 213 is arranged between the terminal elements forming terminals 212 and the first adhesive layer (not shown). The first intermediate element 213 covers the terminal elements forming terminals 212 of the base plate 4 when seen in the axial direction and protects the first adhesive layer from mechanical stress from the terminal elements of the base plate.

As previously described, some parts of the illustrated base plate 4, can be provided as a separate patch to be applied to an existing base plate, e.g. comprising one or more of the components as described, such as to provide a base plate like the base plate 4 as described. For example, a sensor patch 700 can be provided, e.g. comprising the electrode assembly 204, the first connector 211, the first intermediate element 213, the first adhesive layer 200 and the release liner 206. Additionally, the sensor patch 700 can also comprise the second adhesive layer 202 and/or the top layer 208. It may be envisioned that the user can provide a hole in layers of the base plate whereto the sensor patch 700 is to be applied, to allow for the first connector 211 of the sensor patch 700 to protrude through layers of the base plate whereto the sensor patch 700 is applied. Alternatively, the sensor patch 700 can be applied to the base plate such that the first connector 211 is positioned outside the periphery of the base plate.

Figure 4:
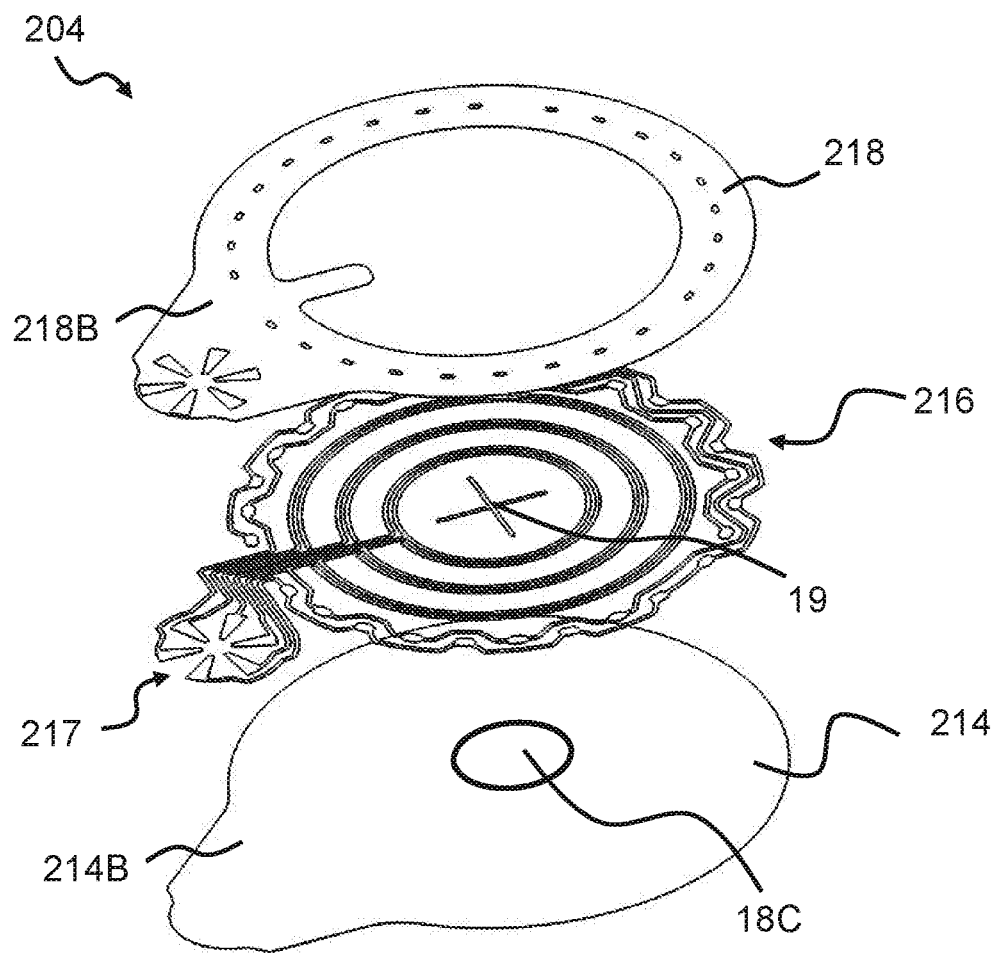
FIG. 4 illustrates an exploded view of an exemplary electrode assembly.

FIG. 4 illustrates an exploded view of an exemplary electrode assembly 204 of a base plate and/or sensor patch. The electrode assembly 204 has a distal side 204A and a proximal side 204B. The electrode assembly 204 comprises a support layer 214 with proximal surface 214B and electrodes 216 arranged on the proximal side of the support layer 214 and including a ground electrode, a first electrode, a second electrode, a third electrode, a fourth electrode, and a fifth electrode, wherein each electrode has a respective connection part 217 for connecting the electrodes 216 to respective terminal elements of the monitor interface. The electrodes 216 are positioned and/or formed on a proximal side 214B of the support layer 214. Further, electrode assembly 204 comprises a masking element 218 with proximal surface 218B and configured to insulate electrode parts of electrodes 216 from the first adhesive layer of the base plate and/or the sensor patch. The masking element 218 covers or overlap with parts of the electrodes 216 when seen in the axial direction.

Figure 5:
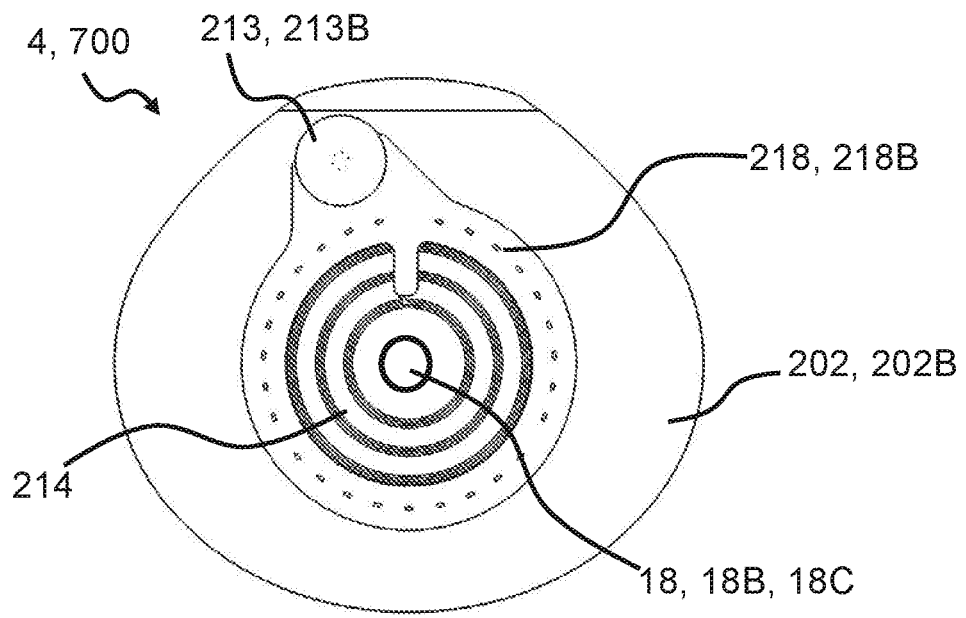
FIG. 5 illustrates a proximal view of parts of a base plate and/or sensor patch.

FIG. 5 is a proximal view of proximal surfaces of base plate parts of the base plate and/or the sensor patch without the first adhesive layer and the release liner. The base plate 4 and/or the sensor patch 700 comprises a first intermediate element 213 on the proximal side of the electrode assembly, i.e. between the electrode assembly 204 and the first adhesive layer (not shown). The first intermediate element 213 covers the terminal elements of the base plate 4 when seen in the axial direction and protects the first adhesive layer from mechanical stress from the terminal elements of the base plate and/or the sensor patch.

Figure 6:
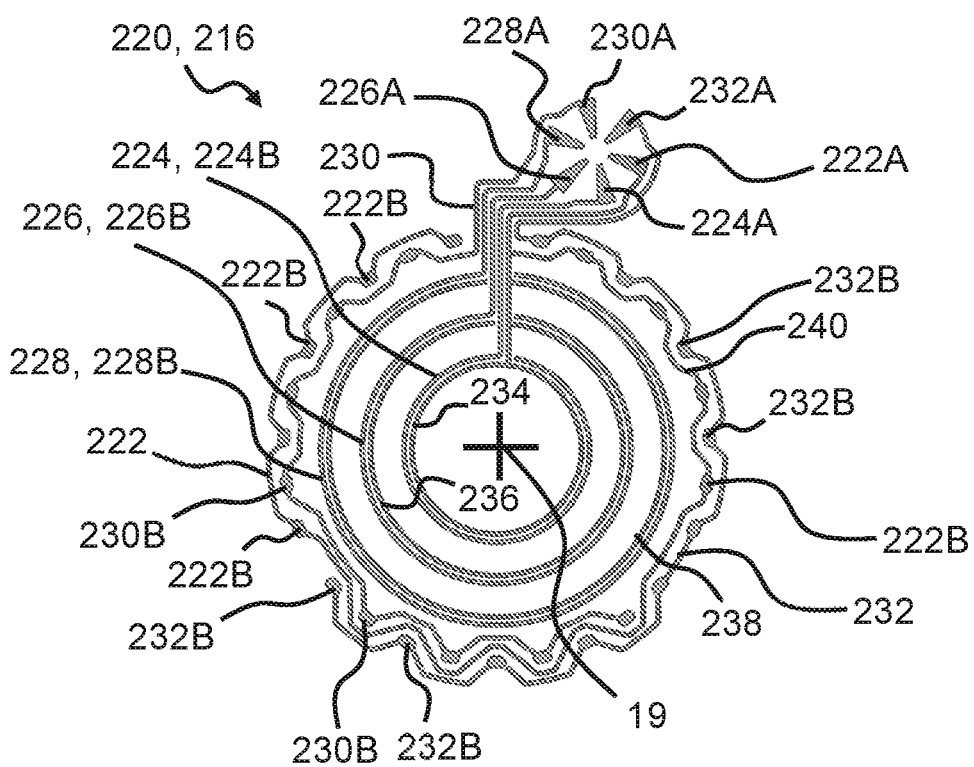
FIG. 6 illustrates a distal view of an exemplary electrode configuration.

FIG. 6 is a distal view of an exemplary electrode configuration 220 of electrodes 216 of the electrode assembly 204. The electrode assembly 204, such as the electrode configuration 220 of the electrode assembly 204 comprises a ground electrode 222, a first electrode 224, a second electrode 226, a third electrode 228, a fourth electrode 230, and a fifth electrode 232. The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 230 comprises a fourth connection part 230A and the fifth electrode 232 comprise a fifth connection part 232A.

The fourth electrode (second leakage electrode) 230 comprises fourth sensing parts 230B. The fifth electrode (third leakage electrode) 232 comprises fifth sensing parts 232B.

The ground electrode 222 comprises a first electrode part 234 for forming a ground or reference for the first electrode 224. The ground electrode 222 comprises a second electrode part 236 for forming a ground or reference for the second electrode 226. The ground electrode 222 comprises a third electrode part 238 for forming a ground or reference for the third electrode 228. The masking element 218 is arranged proximal to the electrodes 222, 224, 226, 228 covering and insulating parts of the electrodes from the first adhesive and forming respective conductor parts of the electrodes 222, 224, 226, 228. The parts of the electrodes 222, 224, 226, 228 not covered by the masking element 219 contacts the first adhesive layer and form sensing parts 224B, 226B, 228B of electrodes 224, 226, 228, respectively. Further, the electrode parts 234, 236, 238 form sensing parts of the ground electrode 222.

Figure 11:
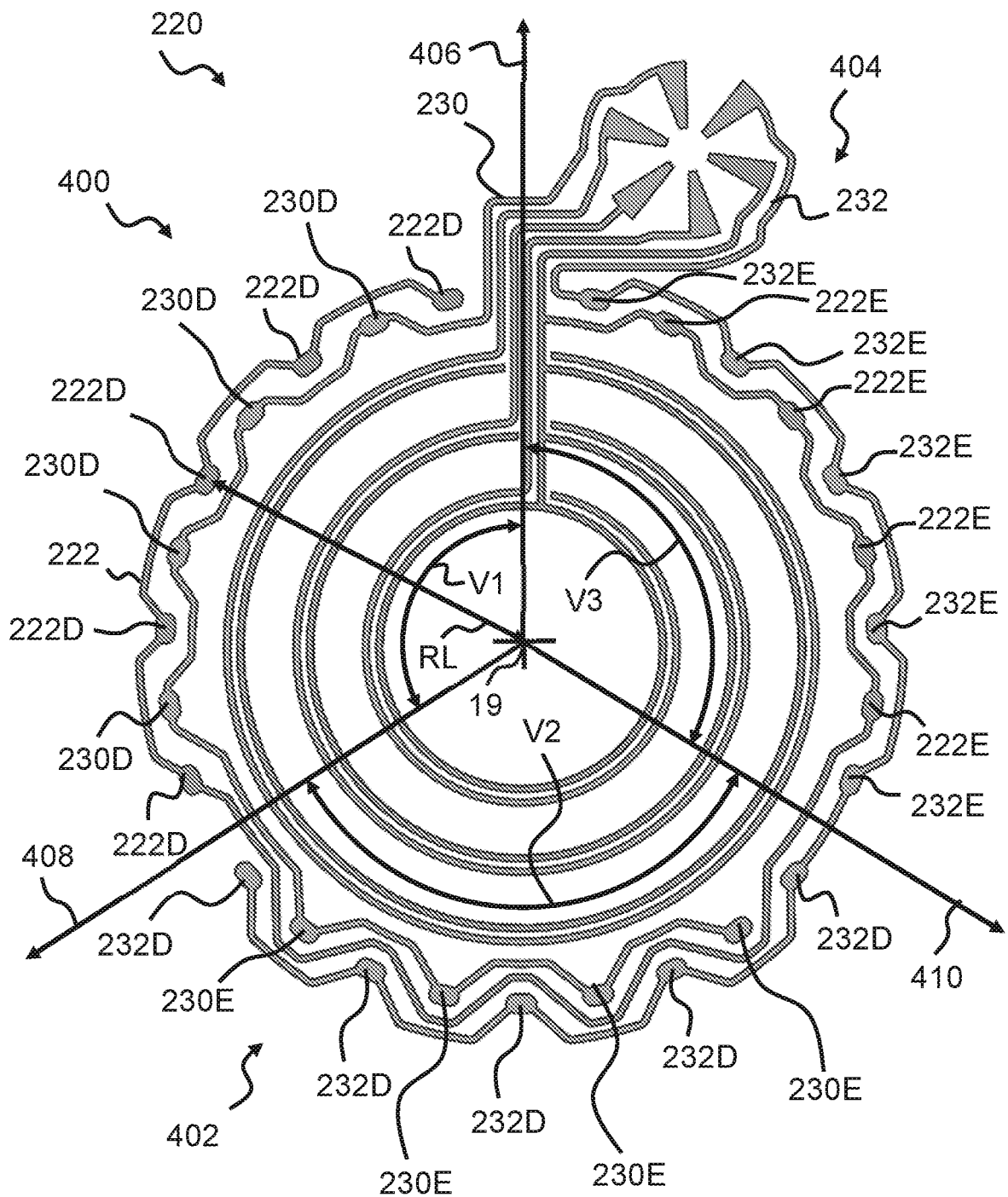
FIG. 11 illustrates a distal view of the electrode configuration of FIG. 6.

The first sensing part 224B extends circularly at least 330 degrees around the stomal opening at a first radial distance R1 from the centre point 19, see also FIG. 11. The first radial distance R1 is 14 mm. The first electrode part 234 is arranged on the inside of the first sensing part (i.e. closer to the centre point) and extends circularly at least 330 degrees around the stomal opening at a first ground distance RG1 from the first sensing part (radially from the centre point). The first ground distance RG1 is about 1 mm.

The second sensing part 226B extends circularly at least 330 degrees around the stomal opening at a second radial distance R2 from the centre point 19, see also FIG. 11. The second radial distance R2 is 18 mm. The second electrode part 236 is arranged on the inside of the second sensing part 226B (i.e. closer to the centre point) and extends circularly at least 330 degrees around the stomal opening at a second ground distance RG2 from the second sensing part 226B (radially from the centre point). The second ground distance RG2 is about 1 mm.

The third sensing part 228B extends circularly at least 330 degrees around the stomal opening at a third radial distance R3 from the centre point 19, see also FIG. 11. The third radial distance R3 is about 26 mm. The third electrode part 238 is arranged on the inside of the third sensing part 228B (i.e. closer to the centre point) and extends circularly at least 330 degrees around the stomal opening at a third ground distance RG3 from the third sensing part 228B (radially from the centre point). The third ground distance RG3 is about 1 mm.

The ground electrode 222 comprises a fourth electrode part 240 for forming a ground or reference for the fourth electrode 230 and the fifth electrode 232. The fourth electrode part 240 of the ground electrode forms the first leakage electrode. The fourth electrode part 240 of the ground electrode 222 extends at least 300 degrees around the stomal opening and comprises ground sensing parts 222B. The fourth sensing parts 230B, fifth sensing parts 232B, and ground sensing parts of the fourth electrode part 240 are circularly distributed around the centre point 19 at a leakage radius from the centre point. The fourth sensing parts 230B, fifth sensing parts 232B, and ground sensing parts of the fourth electrode part may have a radial extension larger than 1.0 mm, such as in the range from 1.5 mm to 3.0 mm, e.g. about 2.0 mm. The fourth sensing parts 230B, fifth sensing parts 232B, and ground sensing parts of the fourth electrode part 240 may have a circumferential extension (perpendicular to the radial extension) larger than 1.0 mm, such as in the range from 2.5 mm to 5.0 mm, e.g. about 3.5 mm. In one or more exemplary base plates and/or sensor patches, the electrodes 224, 226, 228 and electrode parts 234, 236, 238 may be omitted from the electrode configuration/electrode assembly.

Figure 7:
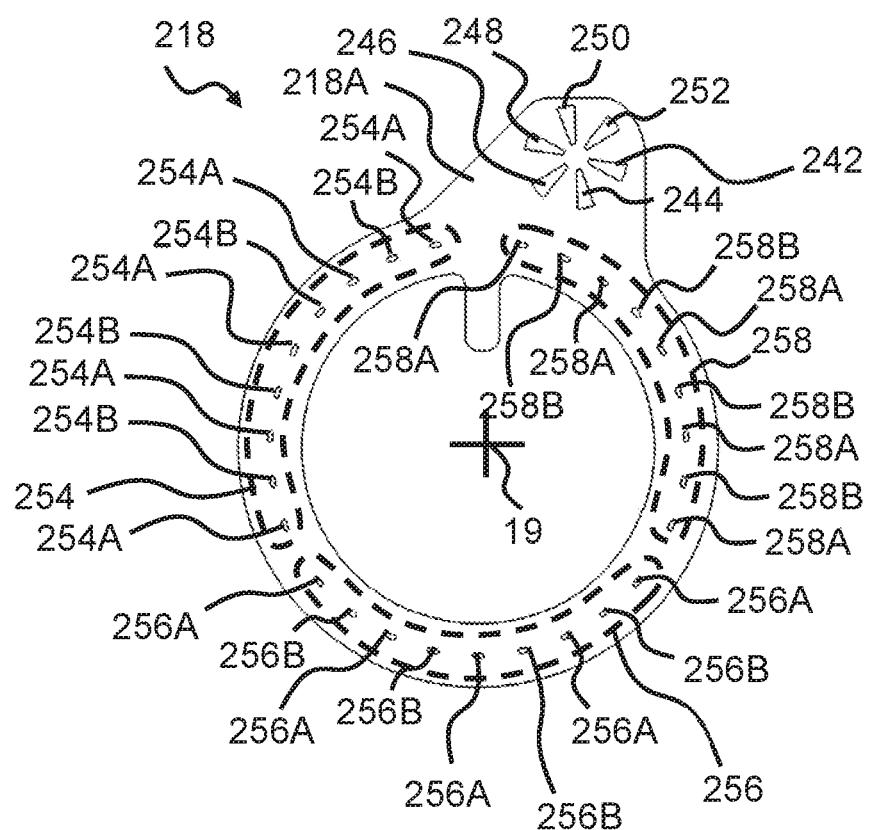
FIG. 7 illustrates a distal view of an exemplary masking element.

FIG. 7 is a distal view of an exemplary masking element. The masking element 218 optionally has a plurality of terminal openings including six terminal openings. The plurality of terminal openings comprises a ground terminal opening 242, a first terminal opening 244, a second terminal opening 246, a third terminal opening 248, a fourth terminal opening 250, and a fifth terminal opening 252. The terminal openings 242, 244, 246, 248, 250, 252 of the masking element 218 are configured to overlap and/or be aligned with respective connection parts 222A, 224A, 226A, 228A, 230A, 232A of the electrodes of the electrode assembly.

The masking element 218 has a plurality of sensor point openings. The sensor point openings comprise primary sensor point openings shown within dotted line 254, each primary sensor point opening configured to overlap a part of the ground electrode (first leakage electrode) 222 and/or a part of the fourth electrode (second leakage electrode) 230. The primary sensor point openings 254 comprise, in the illustrated exemplary masking element, five primary sensor point openings 254A each configured to overlap a respective sensing part of the ground electrode (first leakage electrode) 222. The primary sensor point openings 254 comprise, in the illustrated exemplary masking element, four primary sensor point openings 254B each configured to overlap a respective sensing part of the fourth electrode (second leakage electrode) 230. The sensor point openings comprise secondary sensor point openings shown within dotted line 256, each second sensor point opening configured to overlap a part of the fourth electrode (second leakage electrode) 230 and/or a part of the fifth electrode (third leakage electrode) 232. The secondary sensor point openings 256 comprise, in the illustrated exemplary masking element, five secondary sensor point openings 256A each configured to overlap a respective sensing part of the fifth electrode (third leakage electrode) 232. The secondary sensor point openings 256 comprise, in the illustrated exemplary masking element, four secondary sensor point openings 256B each configured to overlap a respective sensing part of the fourth electrode (second leakage electrode) 230. The sensor point openings comprise tertiary sensor point openings shown within dotted line 258, each tertiary sensor opening configured to overlap a part of the fifth electrode (third leakage electrode) 232 and/or a part of the ground electrode (first leakage electrode) 222. The tertiary sensor point openings 258 comprise, in the illustrated exemplary masking element, five tertiary sensor point openings 258A each configured to overlap a respective sensing part of the fifth electrode (third leakage electrode) 232. The tertiary sensor point openings 258 comprise, in the illustrated exemplary masking element, four tertiary sensor point openings 258B each configured to overlap a respective sensing part of the ground electrode (first leakage electrode) 222. The sensor point openings 254A, 254B, 256A, 256B, 258A, 258B, are circularly arranged at a leakage radius of about 30 mm from the centre point 19.

Figure 8:
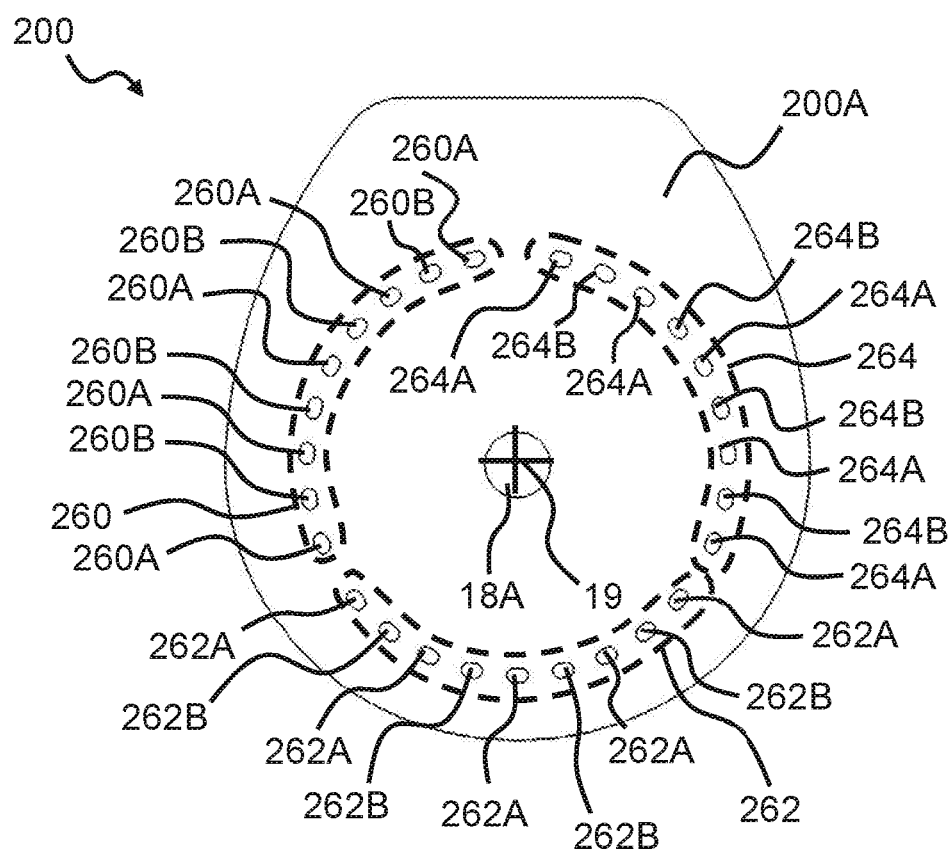
FIG. 8 illustrates a distal view of an exemplary first adhesive layer.

FIG. 8 is a distal view of an exemplary first adhesive layer. The first adhesive layer 200 has a plurality of sensor point openings. The sensor point openings of the first adhesive layer comprise primary sensor point openings shown within dotted line 260, each primary sensor point opening configured to overlap a part of the ground electrode 222 and/or a part of the fourth electrode 230 of the electrode assembly. The primary sensor point openings comprise, in the illustrated exemplary first adhesive layer, five primary sensor point openings 260A each configured to overlap a respective sensing part of the ground electrode 222. The primary sensor point openings comprise, in the illustrated exemplary first adhesive layer, four primary sensor point openings 260B each configured to overlap a respective sensing part of the fourth electrode 230. The sensor point openings of the first adhesive layer comprise secondary sensor point openings shown within dotted line 262, each second sensor point opening configured to overlap a part of the fourth electrode 230 and/or a part of the fifth electrode 232 of the electrode assembly. The secondary sensor point openings comprise, in the illustrated exemplary first adhesive layer, five secondary sensor point openings 262A each configured to overlap a respective sensing part of the fifth electrode 232. The secondary sensor point openings comprise, in the illustrated exemplary first adhesive layer, four secondary sensor point openings 262B each configured to overlap a respective sensing part of the fourth electrode 230. The sensor point openings of the first adhesive layer comprise tertiary sensor point openings shown within dotted line 264, each tertiary sensor opening configured to overlap a part of the fifth electrode 232 and/or a part of the ground electrode 222 of the electrode assembly. The tertiary sensor point openings comprise, in the illustrated exemplary first adhesive layer, five tertiary sensor point openings 264A each configured to overlap a respective sensing part of the fifth electrode 232. The tertiary sensor point openings comprise, in the illustrated exemplary first adhesive layer, four tertiary sensor point openings 264B each configured to overlap a respective sensing part of the ground electrode 222.

Figure 9:
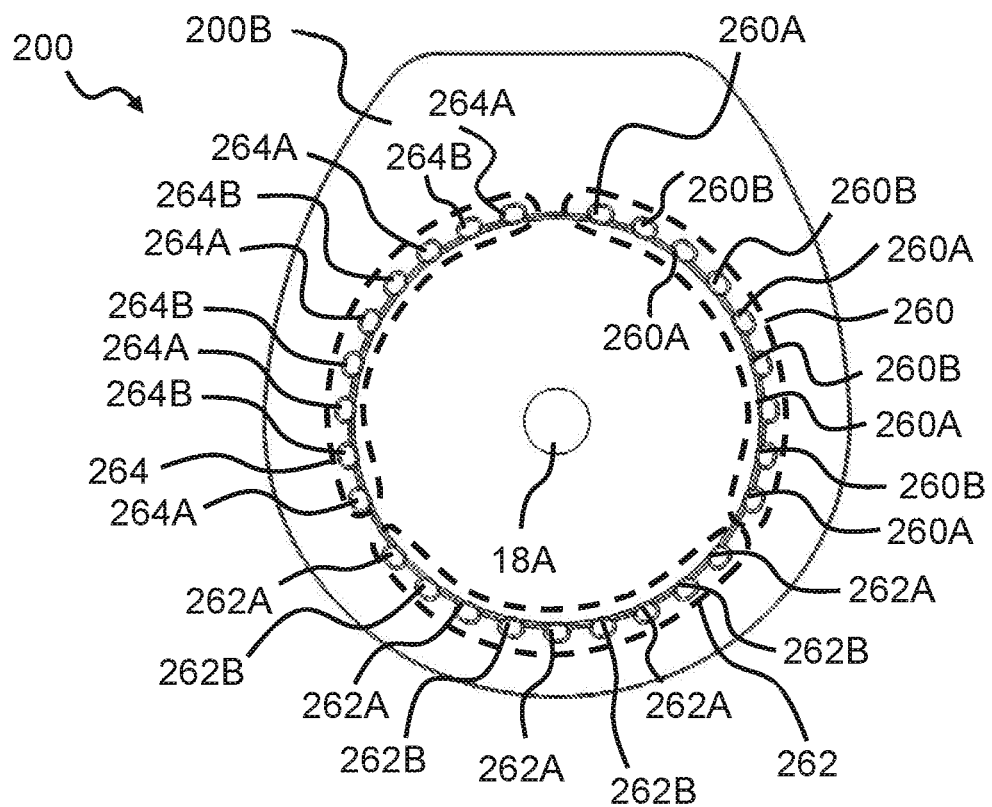
FIG. 9 illustrates a proximal view of the first adhesive layer of FIG. 8.

FIG. 9 is a proximal view of the first adhesive layer of FIG. 8. The sensor point openings 260A, 260B, 262A, 262B, 264A, 264B, are circularly arranged at a leakage radius of about 30 mm from the centre point.

Figure 10:
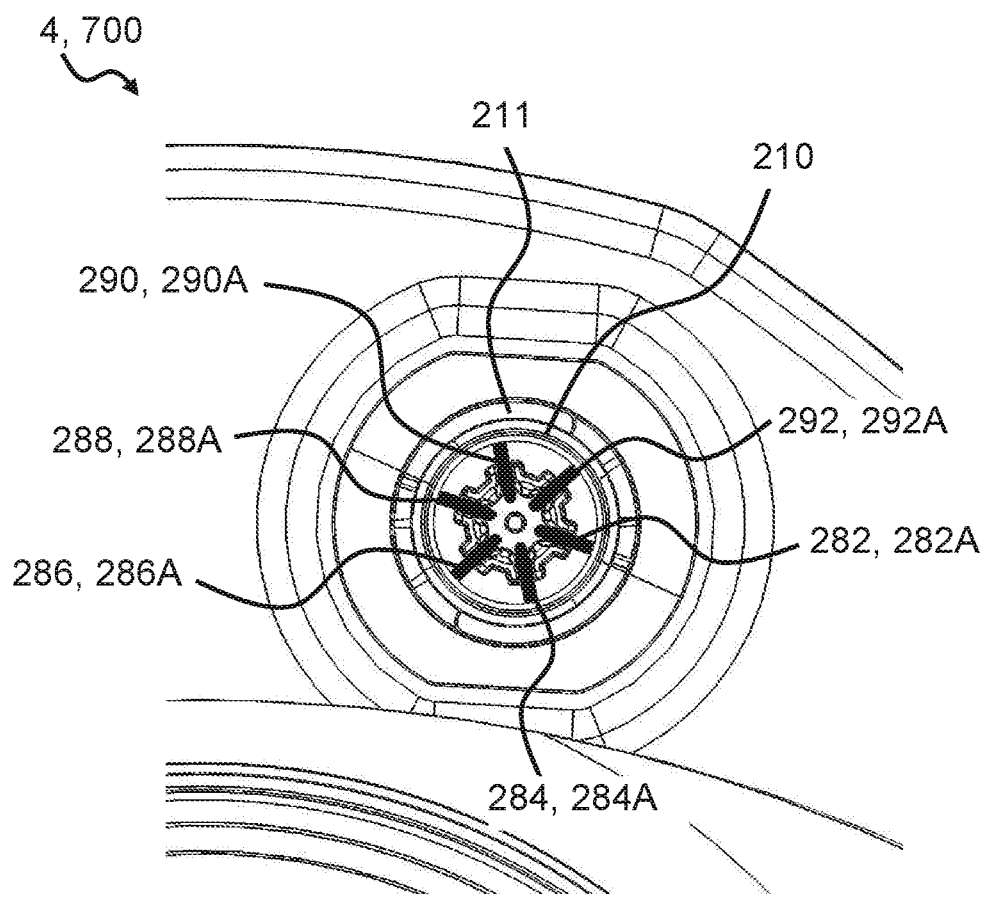
FIG. 10 illustrates a distal view of a part of the base plate and/or sensor patch including a monitor interface.

FIG. 10 is a more detailed distal view of a part of the base plate 4 and/or the sensor patch 700. The base plate 4 and/or sensor patch 700 comprises a monitor interface. The monitor interface comprises the first connector 211. The first connector 211 comprises coupling part 210 configured to releasably couple the monitor device to the base plate and/or the sensor patch and thus forming a releasable coupling. The first connector 211 of the monitor interface comprises a plurality of terminals formed by respective terminal elements for forming respective electrical connections with respective terminals of the monitor device.

The plurality of terminals of the first connector 211 of the monitor interface comprises a ground terminal element 282 forming a ground terminal 282A, a first terminal element 284 forming a first terminal 284, a second terminal element 286 forming a second terminal 286A, and optionally a third terminal element 288 forming a third terminal 288A. The monitor interface optionally comprises a fourth terminal element 290 forming a fourth terminal 290A and/or a fifth terminal element 292 forming a fifth terminal 292A. The terminal elements 282, 284, 286, 288, 290, 292 contact respective connection parts 222A, 224A, 226A, 228A, 230a, 232A of electrodes 222, 224, 226, 228, 230, 232.

The position of the first connector on the base plate and/or the sensor patch, the number of terminals and the position of the terminals in the coupling part can be adapted to the electrode configuration used in the electrode assembly of the base plate and/or the sensor patch. For example, a first connector for a base plate and/or a sensor patch with the electrode configuration 220A shown in FIG. 11 comprises four terminals respectively connected to connection parts 222A, 224A, 226A, 228A of the electrodes, and a first connector for a base plate and/or a sensor patch with the electrode configuration 220B shown in FIG. 12 comprises three terminals respectively connected to connection parts 222A, 224A, 226A of the electrodes.

The first connector can be arranged in a neck portion of the base plate and/or sensor patch. The neck portion can be an integral part of the first and/or second adhesive layer and extend radially away from the stomal opening. Thus, the neck portion is adapted for adhesion onto the skin of the user.

FIG. 11 is a distal view of the exemplary electrode configuration 220 of FIG. 6 for a base plate and/or a sensor patch. The electrode configuration 220 comprises a first leakage electrode 222, second leakage electrode 230, and third leakage electrode 232. The leakage electrodes 222, 230, 232 are configured to detect presence of fluid on the proximal side of the first adhesive layer in three sensing zones (three angular sensing zones, in the illustrated example), primary sensing zone 400, secondary sensing zone 402, and tertiary sensing zone 404. The primary sensing zone 400 is arranged in a primary angle space between a first direction 406 and a second direction 408 from the centre point 19, wherein the primary angle space spans a primary angle V1 of 120°. The secondary sensing zone 402 is arranged in a secondary angle space between the second direction 408 and a third direction 410 from the centre point 19, wherein the secondary angle space spans a secondary angle V2 of 120°. The tertiary sensing zone 404 is arranged in a tertiary angle space between the third direction 410 and the first direction 406 from the centre point 19, wherein the tertiary angle space spans a tertiary angle V3 of 120°.

The first leakage electrode 222 comprises five primary sensing parts 222D arranged in the primary sensing zone 400, and four tertiary sensing parts 222E arranged in the tertiary sensing zone 404. Each primary sensing part 222D is aligned with a respective primary sensor point opening 254A of the masking element 218 (see FIG. 7). Further, each primary sensing part 222D is aligned with a respective primary sensor point opening 260A of the first adhesive layer 200 (see FIG. 8). Each tertiary sensing part 222E of the first leakage electrode 222 is aligned with a respective tertiary sensor point opening 258B of the masking element 218 (see FIG. 7). Further, each tertiary first sensing part 222E is aligned with a respective tertiary sensor point opening 264B of the first adhesive layer 200 (see FIG. 8).

The second leakage electrode 230 comprises four primary sensing parts 230D arranged in the primary sensing zone 400, and four secondary sensing parts 230E arranged in the secondary sensing zone 402. Each primary sensing part 230D is aligned with a respective primary sensor point opening 254B of the masking element 218 (see FIG. 7). Further, each primary sensing part 230D is aligned with a respective primary sensor point opening 260B of the first adhesive layer 200 (see FIG. 8). Each secondary sensing part 230E is aligned with a respective secondary sensor point opening 256B of the masking element 218 (see FIG. 7). Further, each secondary sensing part 230E is aligned with a respective secondary sensor point opening 262B of the first adhesive layer 200 (see FIG. 8).

The third leakage electrode 232 comprises five secondary sensing parts 232D arranged in the secondary sensing zone 402, and five tertiary sensing parts 232E arranged in the tertiary sensing zone 404. Each secondary sensing part 232D is aligned with a respective secondary sensor point opening 256A of the masking element 218 (see FIG. 7). Further, each secondary sensing part 232D is aligned with a respective secondary sensor point opening 262A of the first adhesive layer 200 (see FIG. 8). Each tertiary sensing part 232E is aligned with a respective tertiary sensor point opening 258A of the masking element 218 (see FIG. 7). Further, each tertiary sensing part 232E is aligned with a respective tertiary sensor point opening 264A of the first adhesive layer 200 (see FIG. 8).

The sensing parts 222D, 222E, 230D, 230E, 232D, 232E are circularly arranged at a leakage radius RL of about 30 mm from the centre point.

Figure 12:
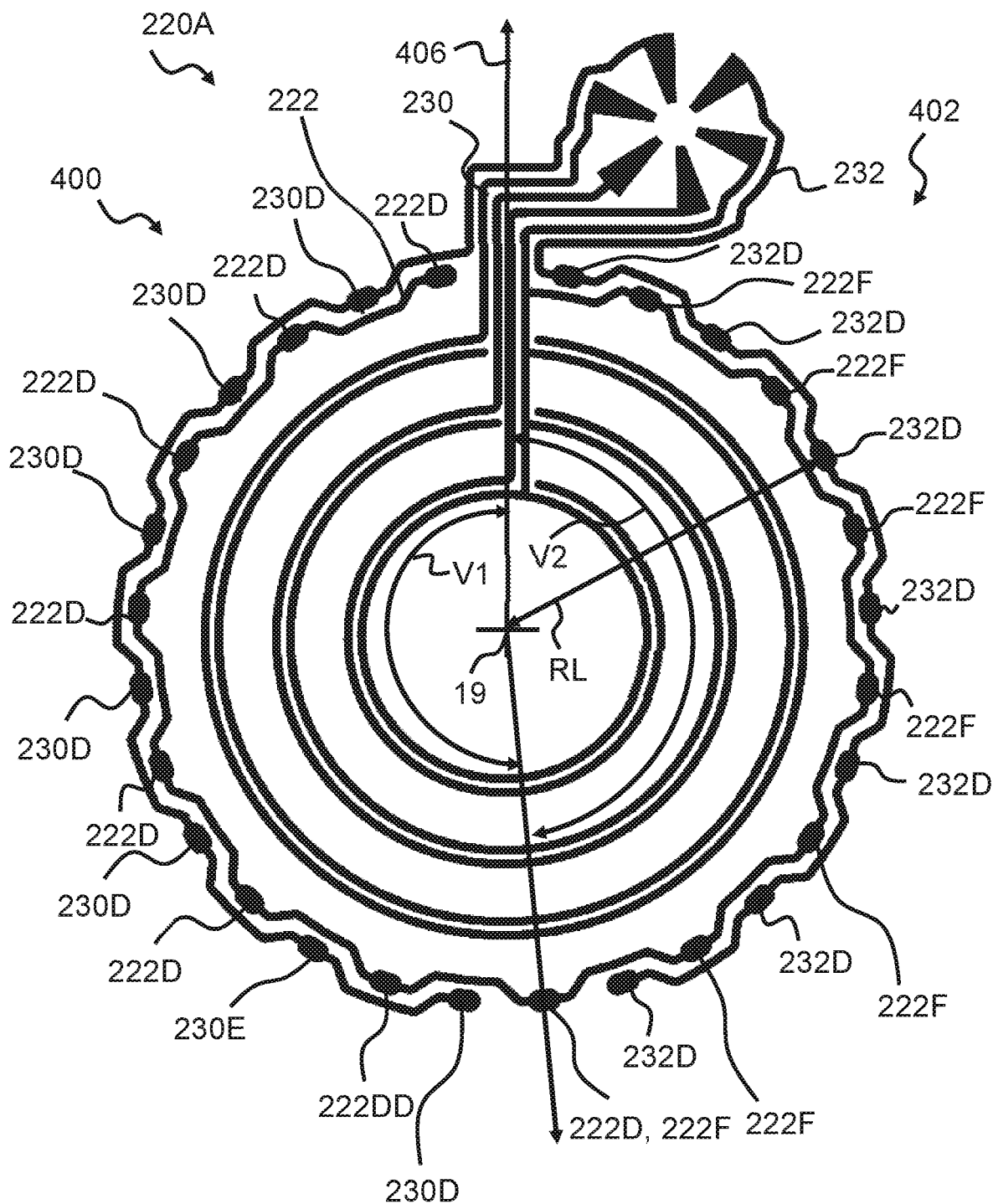
FIG. 12 illustrates a distal view of an exemplary electrode configuration.

FIG. 12 is a distal view of an exemplary electrode configuration 220A for a base plate and/or a sensor patch.

The electrode configuration 220 comprises a first leakage electrode 222, second leakage electrode 230, and third leakage electrode 232. The leakage electrodes 222, 230, 232 are configured to detect presence of fluid on the proximal side of the first adhesive layer in two angular sensing zones, primary sensing zone 400 and secondary sensing zone 402. The primary sensing zone 400 is arranged in a primary angle space between a first direction 406 and a second direction 408 from the centre point 19, wherein the primary angle space spans a primary angle V1 of about 185°. The secondary sensing zone 402 is arranged in a secondary angle space between the second direction 408 and the first direction 406 from the centre point 19, wherein the secondary angle space spans a secondary angle V2 of about 175°.

The first leakage electrode 222 comprises primary sensing parts 222D arranged in the primary sensing zone 400, and secondary sensing parts 222F arranged in the secondary sensing zone 402. The second leakage electrode 230 comprises primary sensing parts 230D arranged in the primary sensing zone 400. The third leakage electrode 232 comprises secondary sensing parts 232D arranged in the secondary sensing zone 402. Each primary sensing part 222D, 230D is aligned with a respective primary sensor point opening of the masking element 219 (see FIG. 13) and with a respective primary sensor point opening of the first adhesive layer 201 (see FIG. 14). The sensing parts 222D, 222F, 230D, and 232D are circularly arranged at a leakage radius RL of about 30 mm from the centre point.

Figure 13:
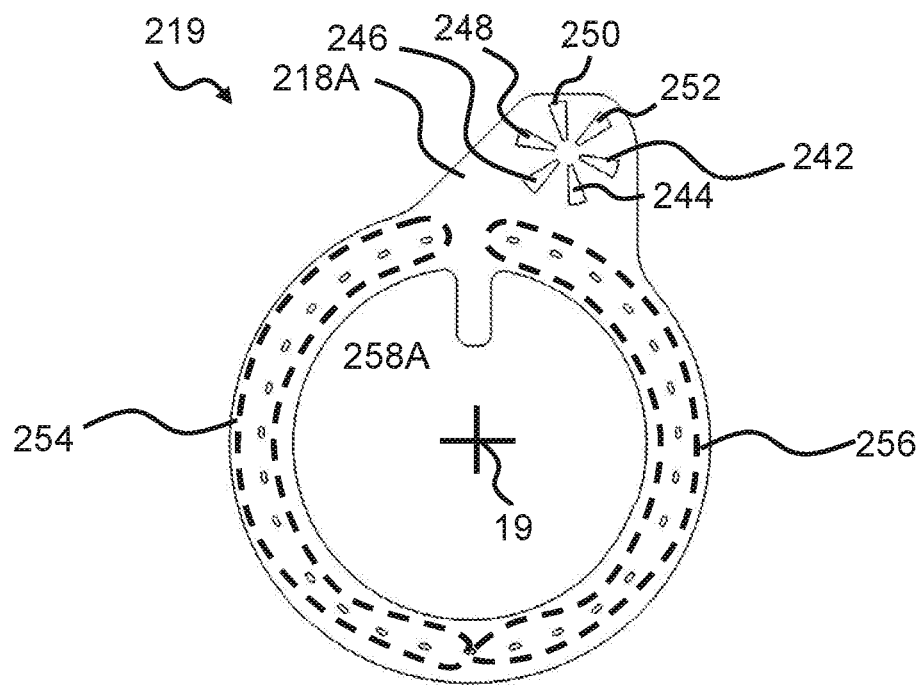
FIG. 13 illustrates a distal view of an exemplary masking element.
Figure 14:
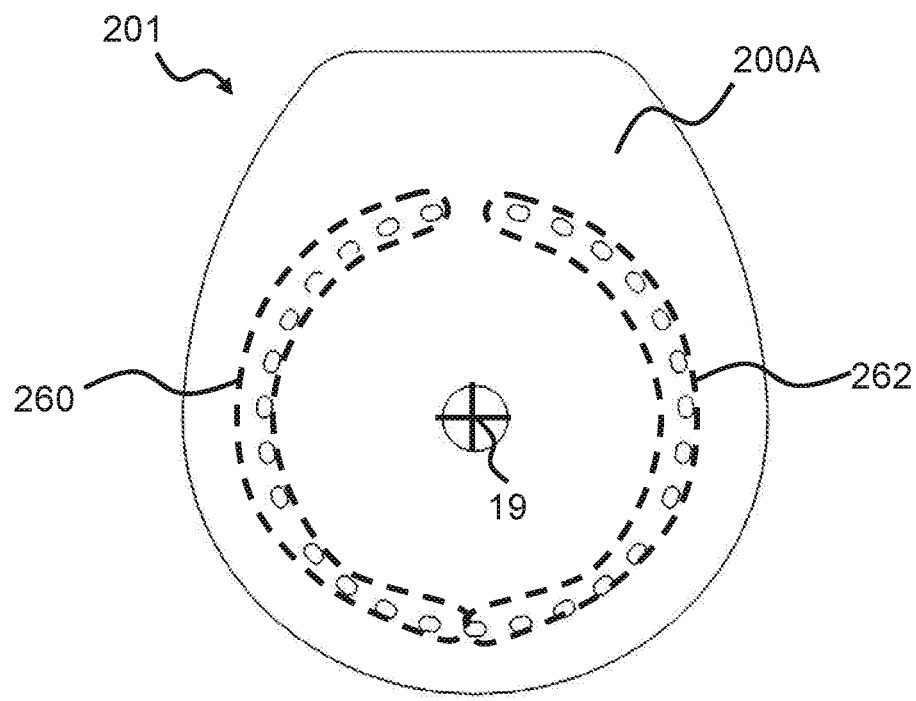
FIG. 14 illustrates a distal view of an exemplary first adhesive layer.

FIG. 13 is a distal view of masking layer 219 for electrode configuration 220A in FIG. 12. The masking layer 219 comprises primary sensor point openings 254 and secondary sensor point openings 256. FIG. 14 is a distal view of first adhesive layer 201 for electrode configuration 220A in FIG. 12 implementing a base plate and/or a sensor patch with two sensing zones arranged in separate angle spaces. The masking layer 201 comprises primary sensor point openings 260 and secondary sensor point openings 262.

Figure 15:
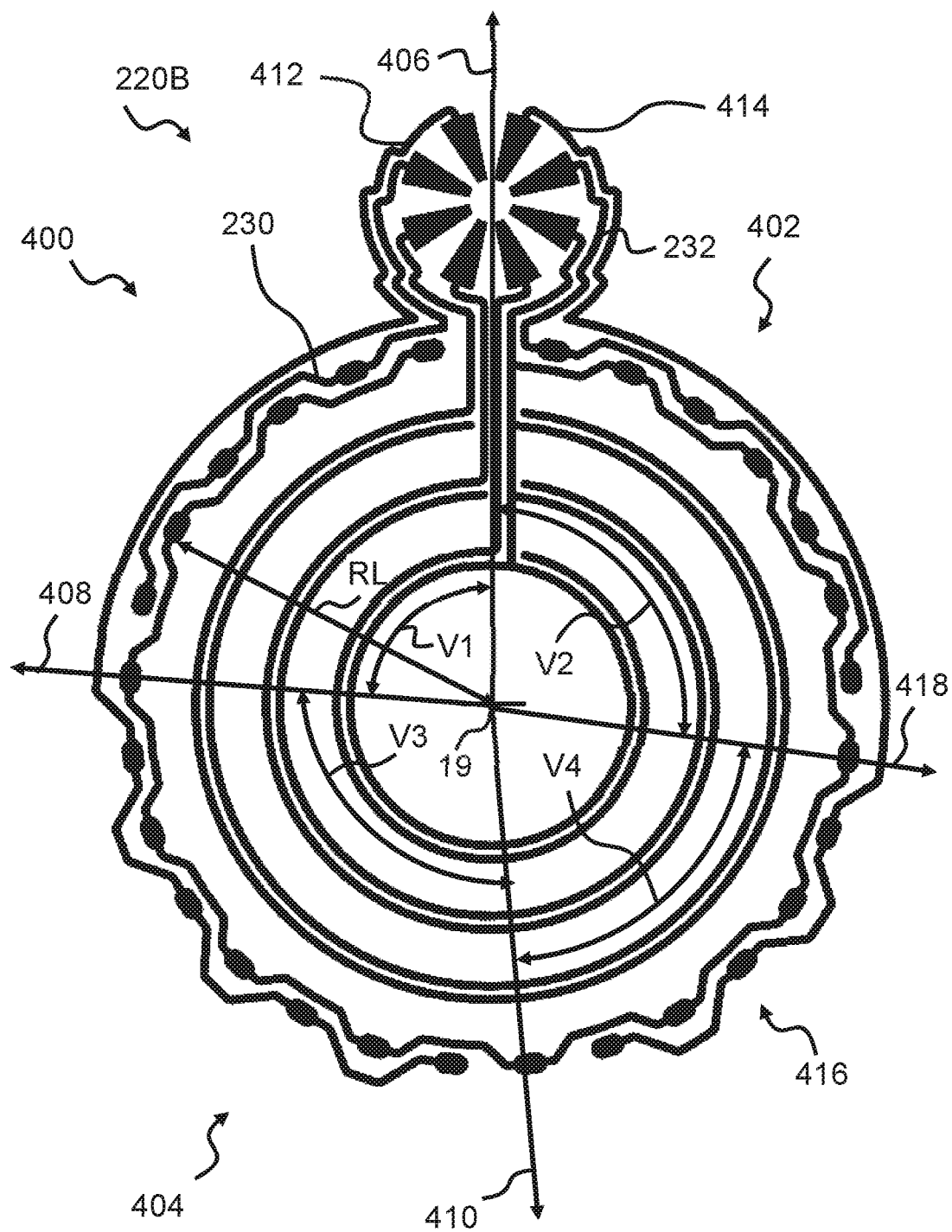
FIG. 15 illustrates a distal view of an exemplary electrode configuration.

FIG. 15 is a distal view of an exemplary electrode configuration 220B for a base plate and/or sensor patch. The electrode configuration 220B comprises first leakage electrode 222, second leakage electrode 230, third leakage electrode 232, fourth leakage electrode 412, and fifth leakage electrode 414. The leakage electrodes 222, 230, 232, 412, 414 are configured to detect presence of fluid on the proximal side of the first adhesive layer in four angular sensing zones 400, 402, 404, 416. The primary sensing zone 400 is arranged in a primary angle space spanning a primary angle V1 of about 85°. The secondary sensing zone 402 is arranged in a secondary angle space spanning a secondary angle V2 of about 95°. The tertiary sensing zone 404 is arranged in a tertiary angle space spanning a tertiary angle V3 of about 95°. The quaternary sensing zone 416 is arranged in a quaternary angle space spanning a quaternary angle V4 of about 85°.

While exemplary base plates and/or sensor patches parts with two, three and four sensing zones have been described in more detail, the base plate and/or the sensor patch can comprise one or a larger number of sensing zones, such as five, six, seven, eight or more sensing zones.

Figure 16:
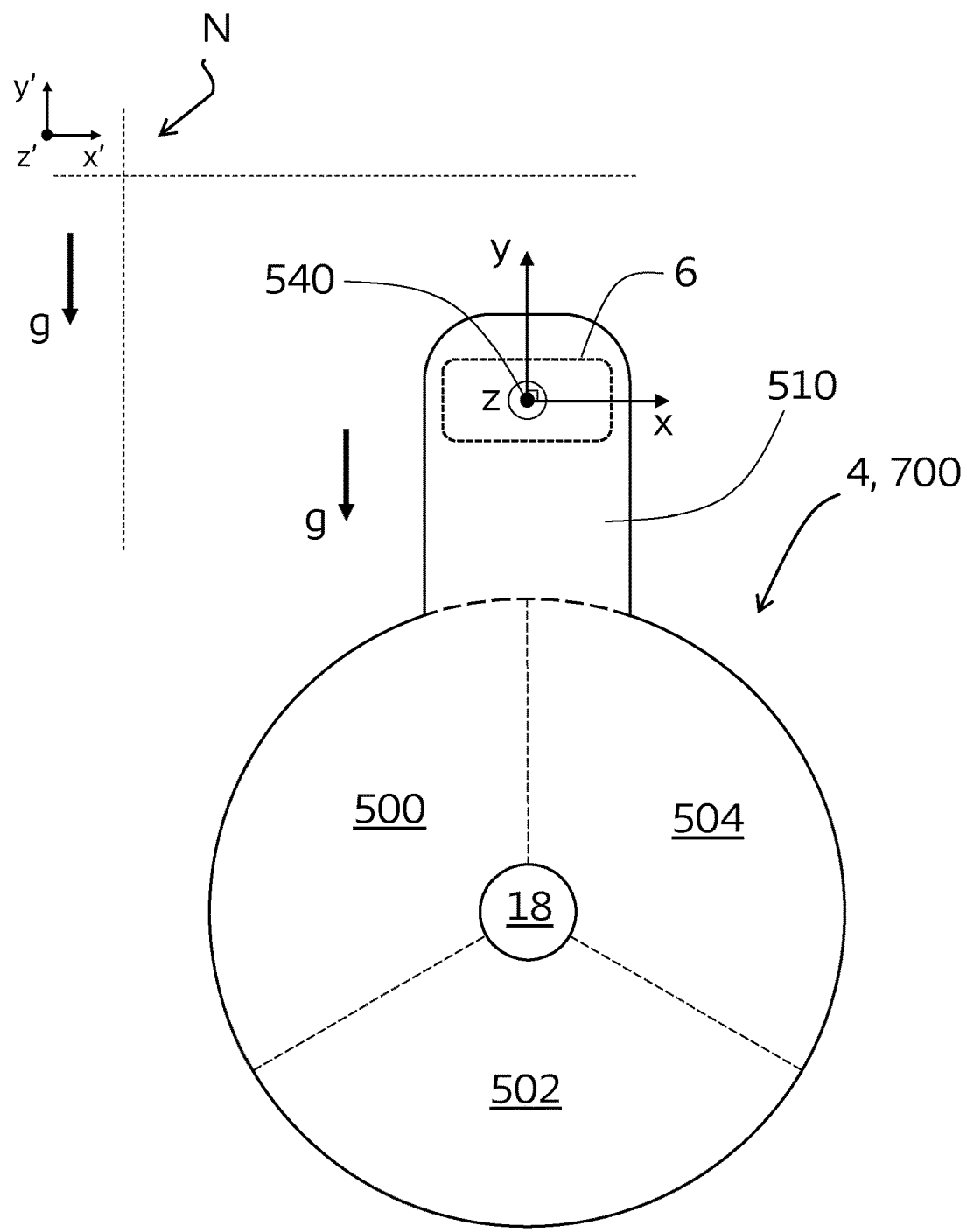
FIG. 16 illustrates an embodiment of a schematic monitor device comprising a 3-axis accelerometer coupled to a schematic base plate and/or sensor patch.

FIG. 16 illustrates a schematic monitor device 6 comprising a 3-axis accelerometer 540 coupled to a schematic base plate 4 and/or sensor patch 700 comprising a neck portion 510 extending radially away from the stomal opening 18 configured to surround an ostomy. The 3-axis accelerometer 540 spans a three-dimensional space (Cartesian coordinate system) as illustrated by the x-axis, y-axis, and z-axis being mutually orthogonal. The direction z-axis is normal to the geometric plane spanned by the x-axis and y-axis. In other words, the accelerometer is capable of measuring movement, such as acceleration, in a three-dimensional space, as spanned by the x-axis, y-axis, and z-axis. In particular, the accelerometer is configured to generate a position signal. The position signal comprises information pertaining to the spatial orientation of the accelerometer 540 and as such of the monitor device 6. The direction of gravity g is illustrated as pointing "downwards". In embodiments, the x-axis, y-axis, and z-axis form/span a local coordinate system relative to the base plate 4 and/or sensor patch 700. In these instances, the x-axis, y-axis, and z-axis are fixed relative to the base plate 4 and/or sensor patch 700 and rotation of the base plate 4 and/or sensor patch 700 corresponds to a rotation of the x-axis, y-axis, and z-axis. Accordingly, the direction of gravity g changes relative to the x-axis, y-axis, and z-axis in response to a change in orientation of the base plate 4 and/or sensor patch 700 (e.g. shown in FIG. 17). In certain configurations, the base plate 4 and/or sensor patch 700 generally span a geometric plane being parallel with the geometric plane spanned by the x-axis and the y-axis of the accelerometer. Alternatively, the base plate 4 and/or sensor patch 700 generally span a geometric plane being parallel with a geometric plane spanned by two of the axes of the accelerometer.

The monitor device 6 is coupled to a base plate 4 and/or sensor patch 700 comprising three sensing zones 500, 502, 504. The sensing zones are provided through adequate arrangement of electrodes as disclosed above and illustrated in e.g. FIGS. 11, 12, and 15. Due to the user being free to apply the base plate 4 and/or sensor patch 700, e.g. taking into account any personal preferences and/or presence of skin folds/scars, the neck portion 510 can take any position (i.e. along 360° circle) about the ostomy about which the base plate 4 and/or sensor patch 700 is configured to be arranged. In the present illustration, the neck portion 510 extends from the base plate 4 and/or sensor patch 700 in a direction being opposite and parallel to the direction of gravity g.

According to embodiments of the invention, the monitor device 6 provides for communicating in which zone of a sensor assembly comprising two or more sensing zones (e.g. sensing zones 500, 502, 504) a possible leakage is occurring. According to embodiments of the invention, the monitor device 6 comprises a 3-axis accelerometer 540 configured to generate a position signal. By providing the monitor device 6 with an accelerometer 540, it is possible to determine a spatial orientation of the monitor device 6 and as such of the base plate 4 and/or sensor patch 700, since the base plate 4 and/or sensor patch 700 are coupled to the monitor device 6. In other words, by the base plate 4 and/or sensor patch 700 being coupled to the monitor device 6, any rotation or spatial orientation of the monitor device 6 is reflected in a similar rotation/spatial orientation of the base plate 4 and/or sensor patch 700.

By defining a natural orientation N of the accelerometer 540, it is possible to determine any deviations/angular offsets from this natural orientation. In embodiments, the natural orientation N can be defined in relation to a global coordinate system including a global x'-axis, y'-axis, and z'-axis. In these instances, the x'-axis, y'-axis, and z'-axis are fixed relative to a rotation of the base plate 4 and/or sensor patch 700. In addition, for example, the natural orientation N can be an orientation wherein the force of gravity along the y'-axis is −1 g, and wherein the force of gravity along the x'-axis and z'-axis is 0 g. According to such definition, the accelerometer 540 is in a natural orientation when the y-axis (of the local coordinate system of the accelerometer) is parallel with y'-axis and the direction of gravity g, and the x-axis, consequently, is parallel to the x'-axis and arranged perpendicular to the direction of gravity g, and as such, is horizontal. The force of gravity being −1 g for the y'-axis is a result of the direction of the y'-axis and can as such be positive (+1 g) if the direction of the y'-axis is flipped, e.g. by a matter of definition. Alternatively, the natural orientation N can be defined as an orientation wherein an angular offset of the x'-axis relative to the direction of gravity g is zero, or wherein an angular offset of the y'-axis relative to the direction of gravity g is zero, or wherein an angular offset of the z'-axis relative to the direction of gravity g is zero. In FIG. 16, the natural orientation N is illustrated by a set of intersecting, dashed lines, one being parallel with to the y'-axis and the direction of gravity g, and one being parallel to the x'-axis and perpendicular to the direction of gravity g.

In FIG. 16, the orientation of the accelerometer 540, and hence of the local coordinate system (i.e. the x-axis, y-axis, and z-axis) and the monitor device and the coupled base plate 4 and/or sensor patch 700, is seen to be aligned with the predefined natural orientation N (e.g., the y-axis is parallel with the direction of gravity g and the y'-axis of the global coordinate system, and hence, the force of gravity along the y-axis is −1 g). Thus, an angular offset, or rotational offset of the base plate 4 and/or sensor patch 700, can be said to be zero. In embodiments, such rotational offset can be communicated (e.g., by transmitting a signal indicative of the rotational offset according to a wireless protocol) to an accessory device, such as a smartphone, in a way to visually illustrate/reflect the physical base plate and/or sensor patch in a graphical user interface, such as in an application (app) of the smartphone. In particular, the visual representation of the physical base plate and/or sensor patch facilitates communicating where (in which sensing zone) a possible leakage is occurring.

Figure 17:
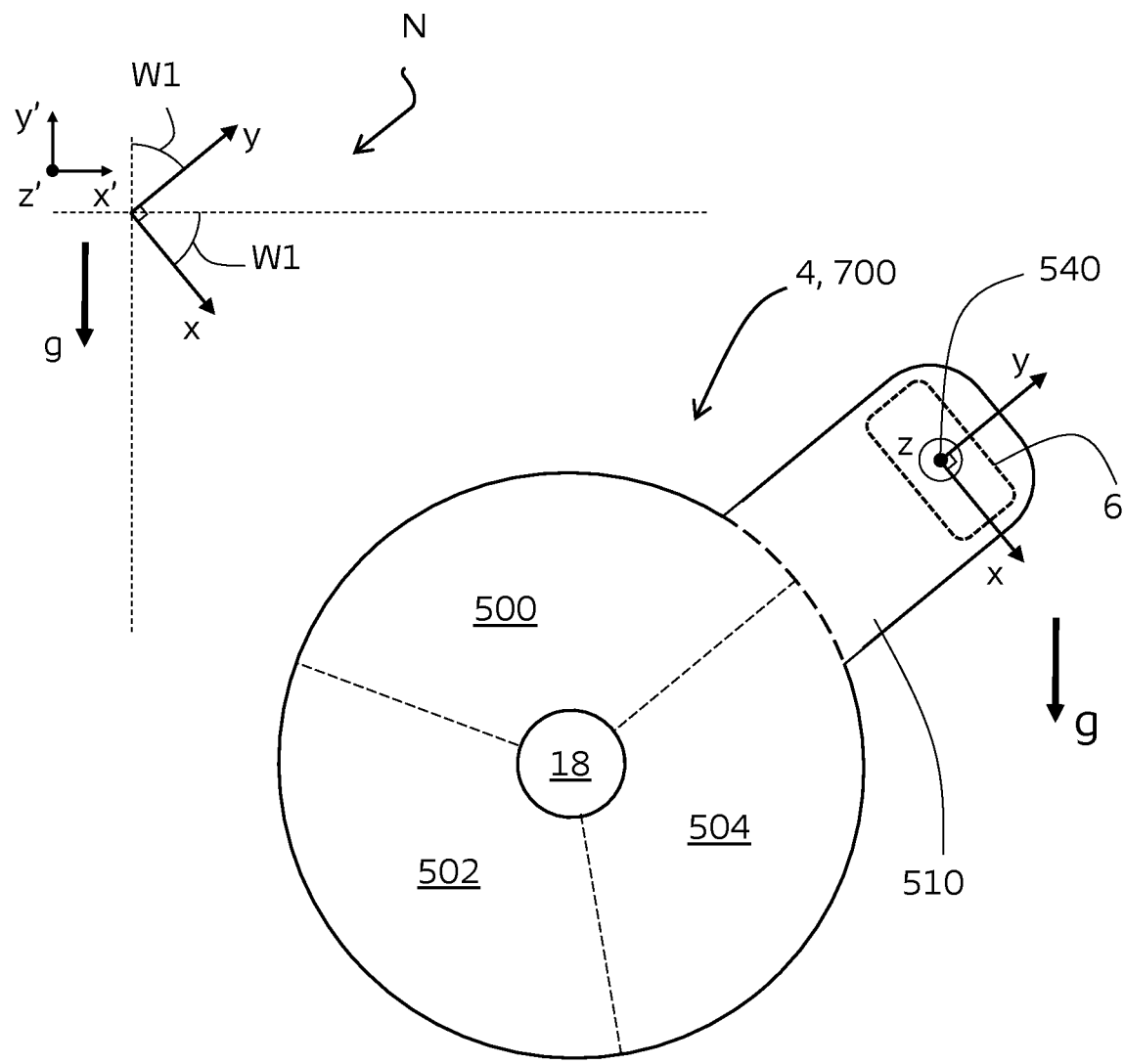
FIG. 17 illustrates an embodiment of a rotated base plate and/or sensor patch coupled with a monitor device.

FIG. 17 illustrates a rotated (relative to a natural orientation N) base plate 4 and/or sensor patch 700 coupled with a monitor device 6 as discussed above in relation to FIG. 16. The axes of the accelerometer 540 are shown to deviate from the natural orientation N and the global coordinate system. To highlight this, the x- and y-axes of the accelerometer 540 have been translated onto the representation of the natural orientation N. Here, it is easily seen how the y-axis of the now-rotated accelerometer 540 is rotated by an angle (angular offset) of W1 from the direction parallel with the direction of gravity g (i.e. the y'-axis), and how the x-axis of the now-rotated accelerometer 540 is rotated by the same angle (angular offset) of W1 from a direction being perpendicular to the direction of gravity g (i.e., the x'-axis).

In embodiments, the monitor device 6 calculates W1 based on the measurements from the accelerometer 540 once the sum total of the accelerations measured in the x-axis, y-axis, and z-axis equals 1 g in order to determine the base plate 4 and/or sensor patch 700 has stopped moving. Otherwise, in certain instances, the acceleration due to the base plate 4 and/or sensor patch 700 moving and the corresponding measurements sensed by the accelerometer 540 may result in an erroneous calculation for W1. Additionally, or alternatively, the measurements from the accelerometer 540 are transmitted by the monitor device 6 to an accessory device 8 and the accessory device 8 calculates W1.

In certain embodiments, W1 is the angle of rotation in the x-y plane and, even if the z-axis is non-zero relative to the z'-axis of the natural orientation, the angle of the z-axis relative to the z'-axis is ignored by subtracting the acceleration measured in the z-axis from 1 g in order to calculate W1 in the x-y plane.

In other words, FIG. 17 illustrates an orientation of the accelerometer 540, and hence of the monitor device 6 and the coupled base plate 4 and/or sensor patch 700, being tilted/offset by an angle W1 relative to the predefined natural orientation N/the global coordinate system. Thus, the angular offset, or rotational offset of the base plate 4 and/or sensor patch 700, can be said to be W1. In embodiments, such rotational offset can be communicated to an accessory device, such as a smartphone, in a way to visually illustrate/reflect the physical base plate and/or sensor patch in a GUI, such as in an application (app) of the smartphone. In particular, the visual representation of the physical base plate and/or sensor patch facilitates communicating to the user where (in which sensing zone) a possible leakage is occurring.

When, or if, the base plate 4 and/or sensor patch 700 is detected to be rotated by an angle W1 relative to a predefined natural orientation N, such angle W1 is incorporated in the visual representation. Since the base plate 4 and/or sensor patch 700 is provided with a neck portion 510, the user can easily translate the visual representation onto his/her body and vice versa. In other words, the neck portion 510 breaks the symmetry of the possibly substantially circular base plate 4 and/or sensor patch 700. By breaking the symmetry, the neck portion 510 can constitute a reference point for the user when he/she is to locate where (in which sensing zone) a possible leakage is occurring. When the visual representation in the GUI of the accessory device incorporates the rotational offset of, here, W1, he/she attains a better spatial understanding of his/her base plate and/or sensor patch and where the possible leakage is occurring.

Figure 18A:
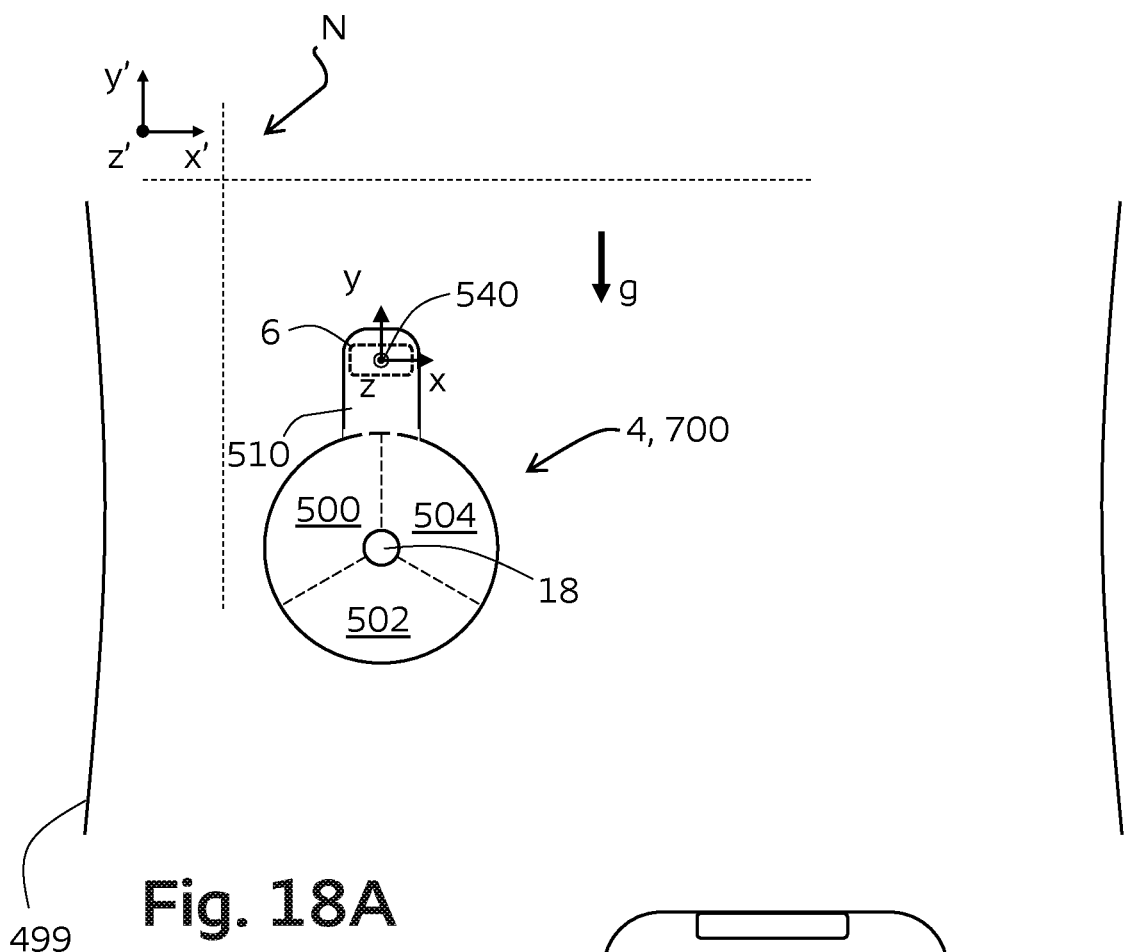
FIG. 18A illustrates an embodiment of a person wearing a base plate and/or sensor patch coupled with a monitor device.

FIG. 18A illustrates a person 499 wearing a base plate 4 and/or sensor patch 700 coupled with a monitor device 6 as described above. The base plate 4 and/or sensor patch 700 comprises three angular spaced sensing zones 500, 502, and 504. Note that the separation of the sensing zones is illustrated by means of dashed lines, but in reality, the sensing zones are separated due to a certain arrangement of electrodes, e.g. as illustrated in FIGS. 11, 12, and 15. The neck portion 510 of the base plate and/or sensor patch is seen to extend radially away from the stomal opening 18 in a direction being parallel with the direction of gravity g. The monitor device 6 comprises an accelerometer 540. A natural orientation N of the accelerometer 540 has been defined according to a previously disclosed definition. According to this definition of the natural orientation N, the monitor device 6, and hence the base plate 4 and/or sensor patch 700, as illustrated does not comprise a rotational offset, since the y-axis of the accelerometer is parallel with the direction of gravity g (in other words, the force of gravity along the y-axis is −1 g) and the x-axis is perpendicular to the direction of gravity g (in other words, the force of gravity along the x-axis is 0 g).

Figure 18B:
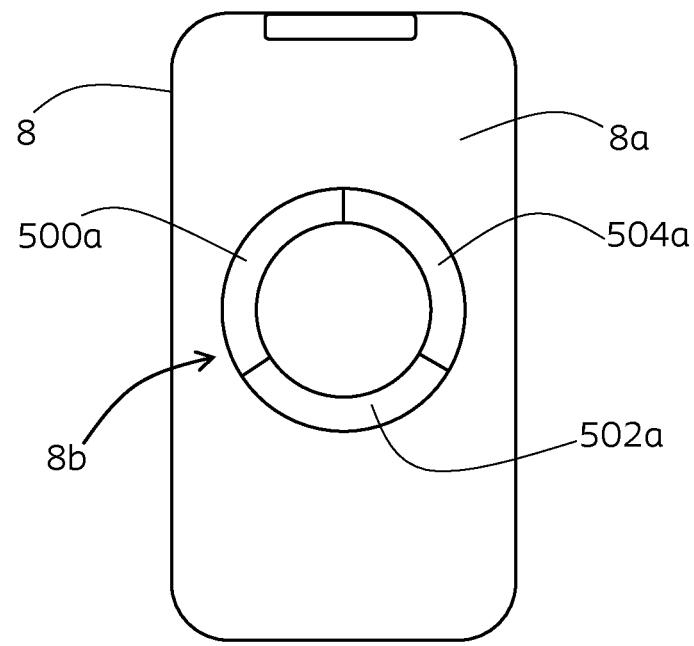
FIG. 18B illustrates an embodiment of an accessory device comprising a visual representation.

Consequently, according to embodiments, the visual representation of the base plate 4 and/or sensor patch 700 does not comprise any rotational offset, as illustrated in FIG. 18B.

FIG. 18B illustrates an accessory device 8 (smartphone) comprising a GUI 8a, such as a screen. The GUI 8a is configured to show a visual representation 8b of the base plate 4 and/or sensor patch 700 as applied to the user's body (see FIG. 18A). In particular, the visual representation illustrates the sensing zones (reference numbers 500, 502, and 504 in FIG. 18A) of the base plate 4 and/or sensor patch 700. The sensing zones can be illustrated by means of ring segments 500a, 502a, 504a. As illustrated, the sensing zones 500, 502, 504 of the base plate 4 and/or sensor patch 700 translates directly onto the visual representation 8b. In particular, the visual representation 8b is oriented such that "up" and "down" are according to the natural orientation of the accessory device 8, or a common understanding of the orientation of the used accessory device 8. In other words, the orientation of the visual representation 8b complies with a normal understanding of the accessory device 8. In further other words, the orientation of the visual representation 8b complies with the orientation of the accessory device 8. For example, where the accessory device 8 is a smartphone, in a portrait orientation, the direction of gravity can be considered to be parallel with a longitudinal direction, e.g. a long edge, of the smartphone. Likewise, in a landscape orientation of the smartphone, the direction of gravity can be considered to be parallel with a short edge of the smartphone. Such orientation complies with a normal understanding of the functionality of a smartphone. Despite a certain visual representation has been described, it will be understood that other visual representations can be employed, including other, such as equivalent, visual representations capable of providing a representation of a leakage state.

Figure 19A:
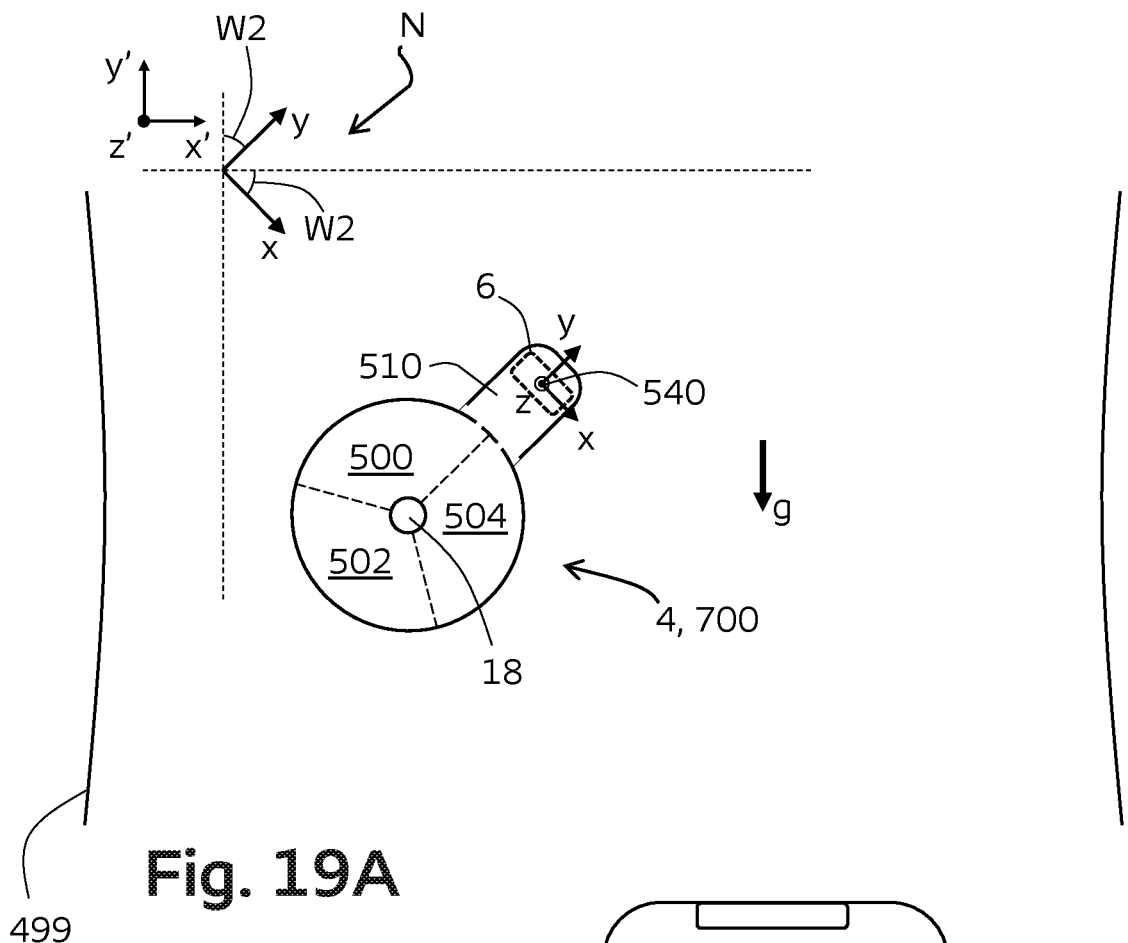
FIG. 19A illustrates an embodiment of a person wearing a base plate and/or sensor patch coupled with a monitor device.

FIG. 19A illustrates a person 499 wearing a base plate 4 and/or sensor patch 700 coupled with a monitor device 6 as described above. The base plate 4 and/or sensor patch 700 comprises three angular spaced sensing zones 500, 502, and 504. The neck portion 510 of the base plate and/or sensor patch is seen to extend radially away from the stomal opening 18 in a direction tilted/deviating from the direction of gravity g. The monitor device 6 comprises an accelerometer 540. A natural orientation N of the accelerometer 540 has been defined according to a previously disclosed definition. According to this definition of the natural orientation N, the monitor device 6, and hence the base plate 4 and/or sensor patch 700, comprises an angular/rotational offset of W2, as highlighted by the translation of the x- and y-axis of the accelerometer 540 onto the natural orientation N.

Figure 19B:
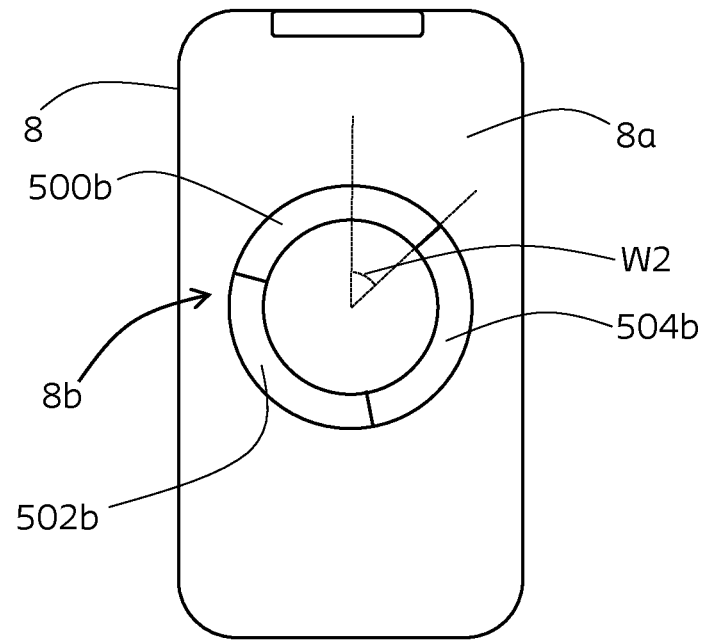
FIG. 19B illustrates an embodiment of an accessory device comprising a visual representation.

FIG. 19B illustrates an accessory device 8 (smartphone) comprising a GUI 8a, such as a screen. The GUI 8a is configured to show a visual representation 8b of the base plate 4 and/or sensor patch 700 as applied to the user's body (see FIG. 19A). As illustrated, the sensing zones 500, 502, 504 of the base plate 4 and/or sensor patch 700 translates directly onto the visual representation 8b, such that the ring segments 500b, 502b, 504b illustrating the sensing zones 500, 502, 504, respectively, are rotated according to the rotational offset W2 of FIG. 19A. The dashed lines/sketched angle in the visual representation 8b are for illustrative purposes here only, and illustrate how the ring segments 500b, 502b, 504b are rotated by the rotational offset of W2.

Figure 20:
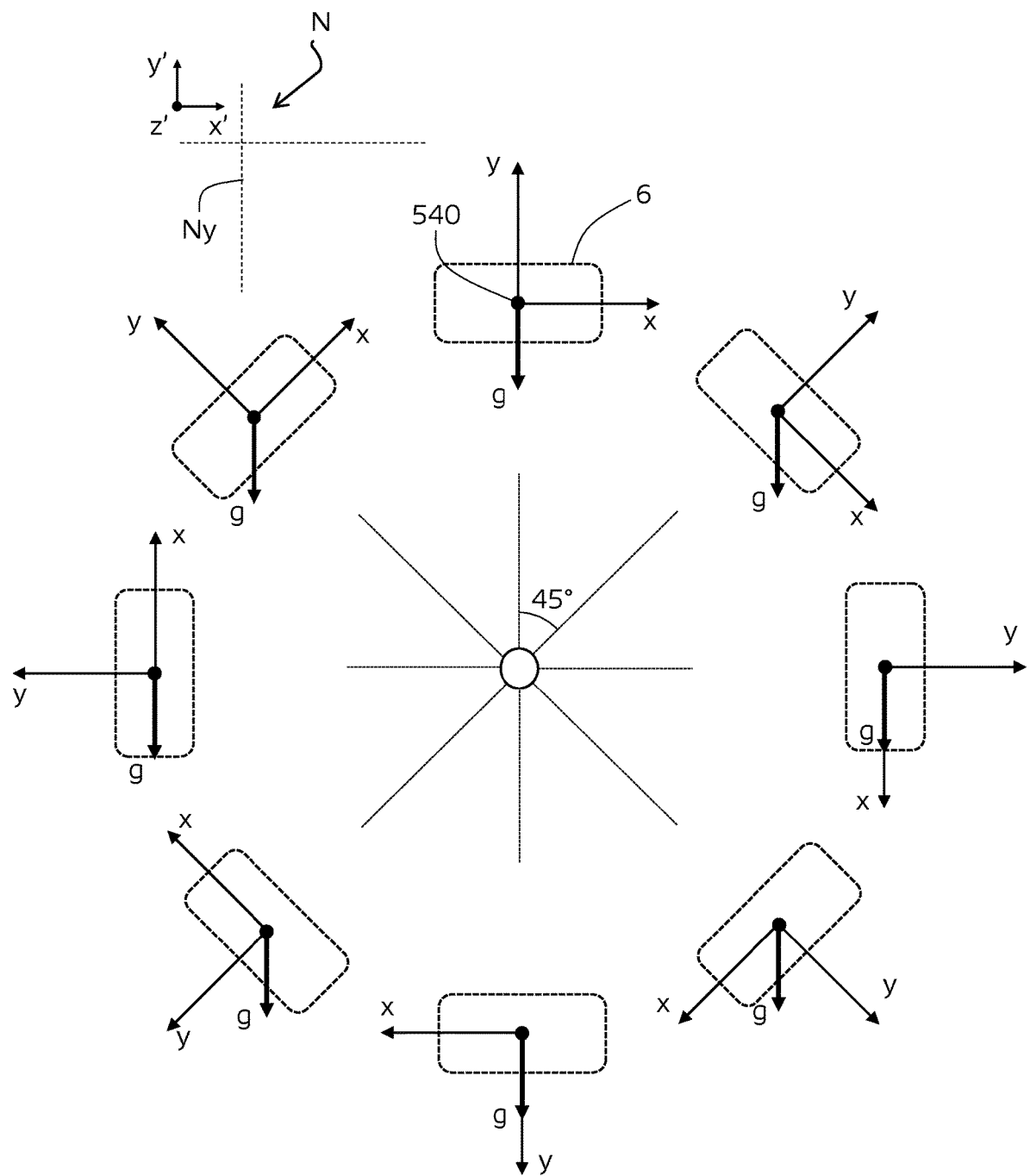
FIG. 20 illustrates eight exemplary orientations of a schematic monitor device comprising a 3-axis accelerometer.

FIG. 20 illustrates eight exemplary orientations of a monitor device 6 comprising a 3-axis accelerometer 540. In particular, FIG. 20 illustrates eight exemplary rotations by which a user can choose to orient his/her base plate and/or sensor patch comprising a plurality of sensing zones. Going in a clockwise direction, the first position is a position wherein the y-axis of the accelerometer is aligned/parallel with the direction of gravity g and the force of gravity along the y-axis is −1 g, such that the angular offset of the y-axis relative to the natural orientation N is zero degrees. The second position is a position wherein the y-axis of the accelerometer is rotated by an angle of 45° from the y-component Ny of the natural orientation N, i.e. the component being aligned/parallel with the direction of gravity. Continuing in the clockwise direction, the orientations of the monitor device are positions wherein the y-axis of the accelerometer is rotated in increments of 45°. In each position, the angular offset can be defined to be the angle between the y-axis of the accelerometer and the y-component Ny of the natural orientation N.

Figure 21:
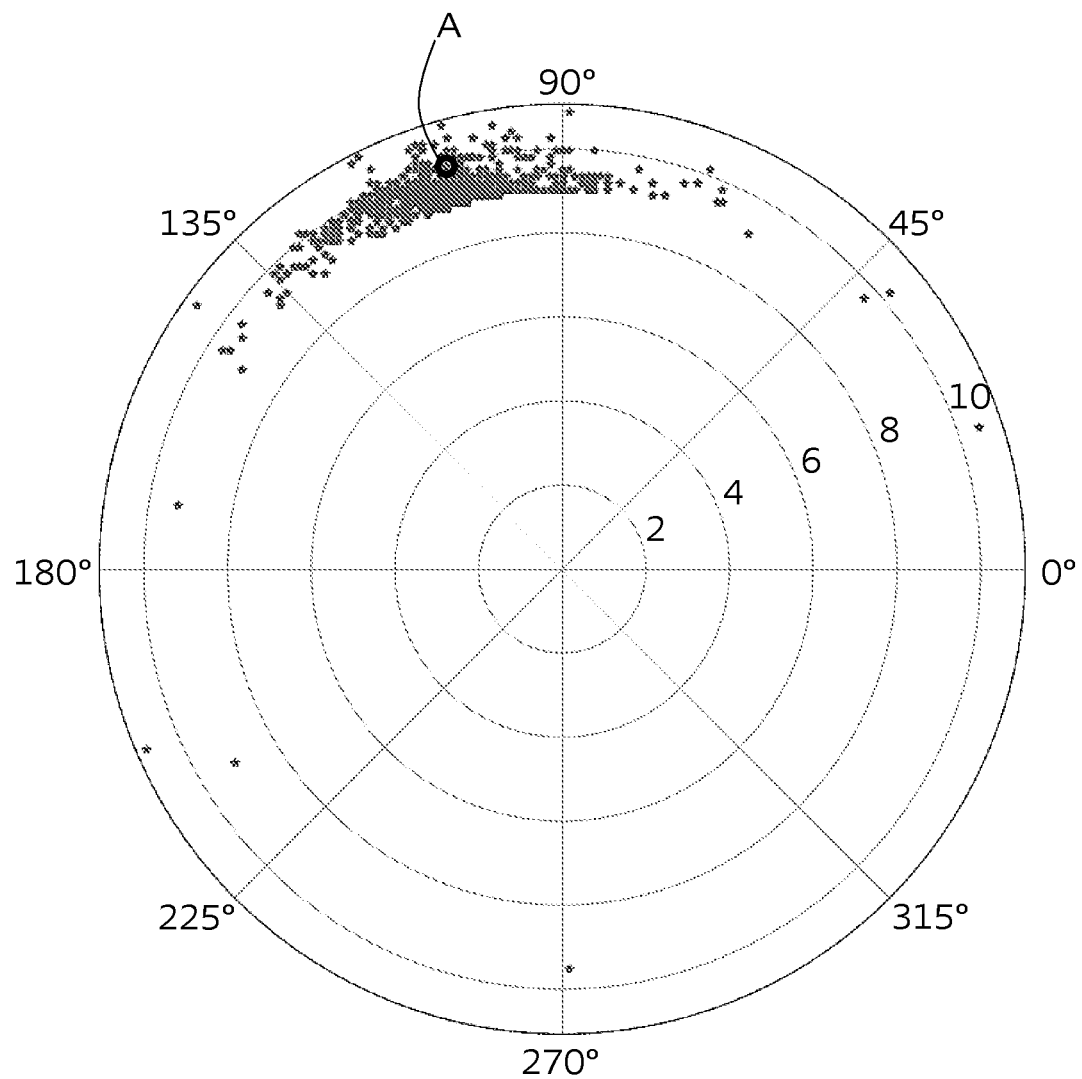
FIG. 21 illustrates a plot of an experimental dataset originating from an accelerometer.

FIG. 21 illustrates a plot of an experimental dataset (position signals) originating from an accelerometer. The accelerometer has been arranged in a monitor device and worn by a human. The plot illustrates a plurality of position signals obtained from the accelerometer over time, each position signal comprising information pertaining to a spatial orientation/angular offset of the accelerometer relative to a natural orientation. The concentric circles illustrate the force of gravity as measured in $m/s^2$, such that 9.8 $m/s^2$=1 g. The (angular) distribution of the data points/position signals indicates that the wearer has been moving around, e.g. walking around. Over time, due to the continued upright position of a walking human, the data points form a trend. In the present case, the data points gather around an average angular offset A of 106°. In other words, the 106° represents the (average) direction of gravity. Thus, data suggests that the monitor device has been worn such that the y- and x-axis of the accelerometer have been tilted 106° relative to the natural orientation of the respective y- and x-axis.

Since the monitor device is supposed to be worn by a human, a way of determining the actual rotational offset of the (adhered) base plate and/or sensor patch is needed. A single assessment of the spatial orientation of the accelerometer relative to a natural orientation can vary greatly, since the wearer can move around, shift his/her weight from leg to leg, jump, bend over, etc. Thus, if one were to determine the spatial orientation of the accelerometer, and hence the rotational offset of the base plate and/or sensor patch, based on a single reading of accelerometer/a single position signal, the wearer would have to stand in perfect, predefined, e.g. upright, position, which is practically impossible. In other words, a single assessment of the spatial orientation is merely indicative of a certain movement of the wearer at a certain point in time. However, by averaging the position signals obtained over a certain amount of time, a trend can be formed. The trend will reveal how the accelerometer, and hence the base plate and/or sensor patch, is fixed relative to the wearer and thus the ostomy. In the exemplary dataset illustrated by the plot in FIG. 21, the average angular offset A is 106°. Hence, despite the wearer is walking around, the monitor device, through the use of the accelerometer, has been able to determine how the monitor device, and hence the base plate and/or sensor patch, is arranged by a sufficient degree of accuracy. The angular offset of 106° is relative to a predefined natural orientation. Thus, the monitor device and hence the base plate and/or sensor patch has been rotated by 106° from the predefined natural orientation. According to embodiments, the angular offset is incorporated in a visual representation of the base plate and/or sensor patch in a graphical user interface of an accessory device as previously described, e.g. in relation to FIGS. 18A-19B. Different movements or positions (e.g. standing, sitting, or laying down) of the wearer can result in different distributions of the position signals. Thereby, it is possible to distinguish such different movements or positions. Thus, the monitor device can double as an activity tracker.

Figure 22:
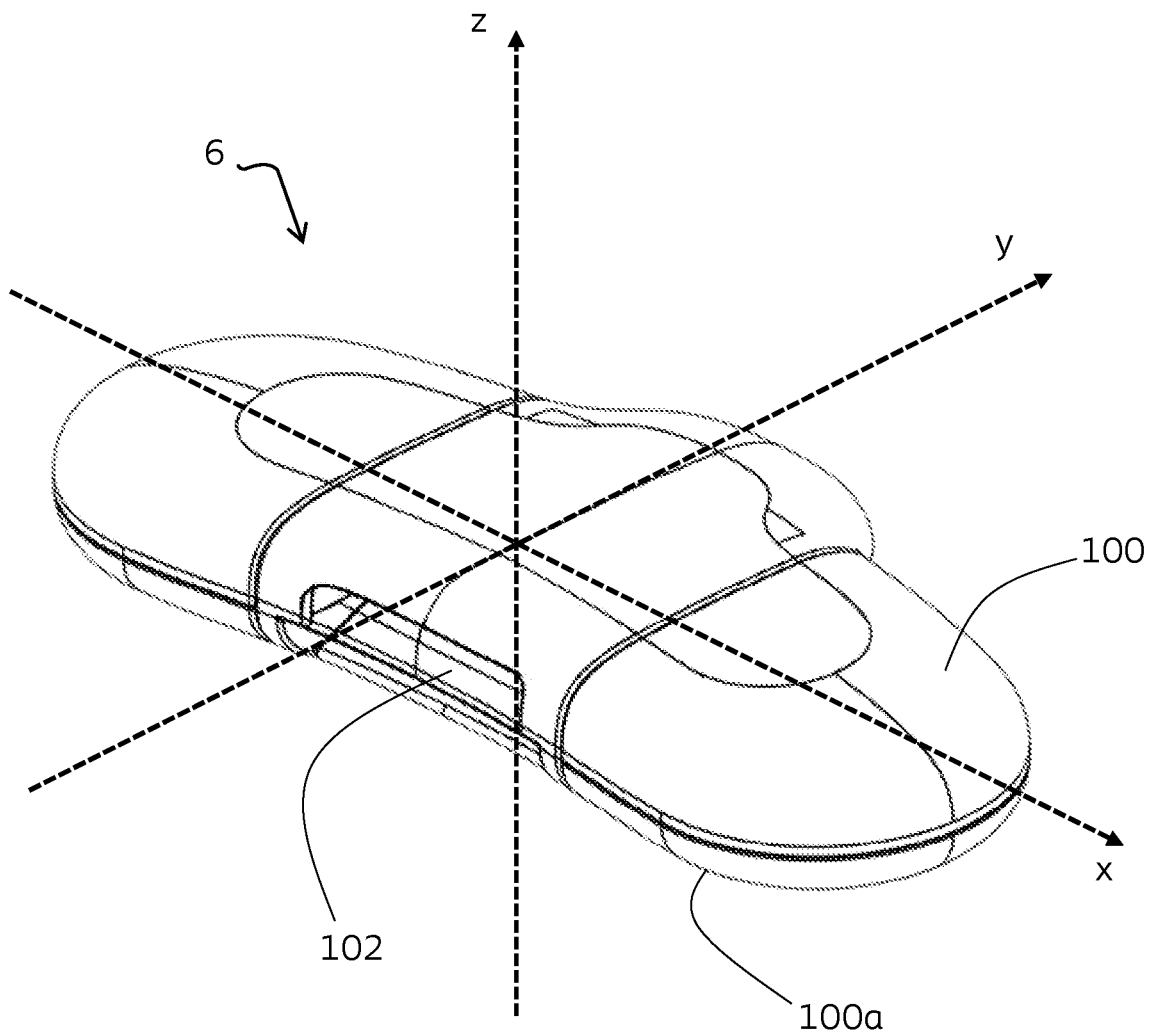
FIG. 22 illustrates an embodiment of a monitor device comprising a 3-axis accelerometer.

FIG. 22 illustrates an exemplary monitor device 6 comprising a housing 100 and an appliance interface 102. The monitor device 6 comprises a processor 101 and a 3-axis accelerometer 540. The accelerometer 540 is capable of measuring movement in a three-dimensional space as spanned by a Cartesian coordinate system and is configured to generate a position signal indicative of a spatial orientation of the monitor device 6. Thus, the accelerometer 540 is capable of measuring acceleration along an x-axis, a y-axis, and a z-axis being mutually orthogonal. In certain embodiments, the axes of the accelerometer extend in the directions as indicated. The housing 100 comprises a skin facing surface 100a. The skin facing surface 100a can be considered substantially planar, such that the surface can flush with the skin or a distal surface of the base plate and/or sensor patch. By flush is meant that the geometric plane defined by the skin facing surface is configured to be substantially parallel with the skin surface above which it is supposed to be worn. In certain embodiments, a geometric plane of the accelerometer, e.g. spanned by its x- and y-axis, is configured to be parallel with such geometric plane defined by the skin facing surface. Thereby is the accelerometer provided with an orientation complying with the embodiments described herein.

Although certain axes and geometric planes of the accelerometer have been assigned certain directions and/or properties throughout the present disclosure, it will be understood that other axes, or even intermediate directions capable of being described by the set of axes (e.g. described on the form (x,y,z)), can be assigned the same certain directions and properties through a simple matter of definition of the coordinate system. For example, where the y-axis is described to be aligned/parallel with the direction of gravity, it will be understood that the x-axis, the z-axis, or an intermediate direction (e.g. described on the form (x,y,z)) can equally well be defined to be the axis aligned/parallel with the direction of gravity. In other words, the coordinate system spanned by the accelerometer can be rotated by any (three-dimensional) angle without this affecting the scope of the invention.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

The invention claimed is:

1. A monitor device for releasable coupling to a sensor assembly of a base plate or a sensor patch for application to a base plate of an ostomy appliance, the monitor device comprising:
   a housing,
   an appliance interface configured for releasably coupling the monitor device to the sensor assembly in a fixed position relative to the sensor assembly, the appliance interface comprising a plurality of terminals for connecting with a plurality of electrodes of the sensor assembly,
   a three-axis accelerometer, wherein the accelerometer is configured to generate a position signal, and
   a processor arranged in said housing configured to determine, based on the position signal of the accelerometer, a spatial orientation of the monitor device relative to an ostomy of a user.

2. The monitor device according to claim 1, wherein the position signal comprises a value for a force of gravity along an x-axis, along a y-axis, and along a z-axis, the axes being mutually orthogonal, and/or a value for a primary angular offset of the x-axis relative to a predefined orientation, a secondary angular offset of the y-axis relative to a predefined orientation, and a tertiary angular offset of the z-axis relative to a predefined orientation.

3. The monitor device according to claim 1, wherein the position signal is sampled at a rate of at least 0.1 Hz.

4. The monitor device according to claim 1, wherein the processor is further configured to determine a spatial orientation of the sensor assembly based on the spatial orientation of the monitor device.

5. The monitor device according to claim 1, wherein the accelerometer comprises a predefined natural orientation, and wherein the primary angular offset of the x-axis relative to the direction of gravity is zero, or the secondary angular offset of the y-axis relative to the direction of gravity is zero, or the tertiary angular offset of the z-axis relative to the direction of gravity is zero.

6. The monitor device according to claim 5, wherein the processor is configured to generate an offset parameter based on an angular offset of the accelerometer from its predefined natural orientation.

7. The monitor device according to claim 1, wherein the accelerometer comprises a predefined natural orientation wherein the force of gravity along the x-axis of the accelerometer is 0 g, and wherein the force of gravity along the y-axis of the accelerometer is −1 g.

8. The monitor device according to claim 1, wherein the spatial orientation relative to the ostomy of the user is determined based on a pattern of movement generated by the user.

9. The monitor device according to claim 8, wherein the pattern of movement comprises a plurality of position signals sampled during a predefined amount of time.

10. The monitor device according to claim 8, wherein the spatial orientation of the monitor device is indicative of a rotational offset of the sensor assembly when the monitor device is coupled to said sensor assembly.

11. The monitor device according to claim 1, wherein the processor is configured to communicate an indication of the spatial orientation to an accessory device.

12. The monitor device according to claim 1, wherein the housing comprises a skin facing surface, and wherein the x-axis and the y-axis of the accelerometer span a geometric plane being substantially parallel with said skin facing surface of the housing, and wherein the z-axis of the accelerometer extends in a direction being normal to said geometrical plane.

13. The monitor device according to claim 1, wherein the appliance interface is configured for coupling to a plurality of electrodes of a sensor assembly, the plurality of electrodes forming at least two sensors arranged in at least two separate sensing zones configured for monitoring a peristomal skin surface.

14. The monitor device according to claim 13, wherein the processor is configured for determining a spatial distribution of the at least two sensing zones based on one or more position signals.

15. The monitor device according to claim 1, wherein the monitor device comprises a memory, and wherein one or more task profiles are stored on the memory, and wherein the monitor device is configured to detect one or more tapping sequences contained in one or more position signals.

16. The monitor device according to claim 15, wherein the processor is configured to compare a given tapping sequence of the one or more tapping sequences with the one or more task profiles and generate an output associated with the given tapping sequence.

17. The monitor device according to claim 16, wherein the output is selected from waking up the monitor device from a sleep mode, activating pairing mode, or to enter sleep mode.

18. The monitor device according to claim 1, wherein the monitor device is configured for turning off or entering a sleep mode if no movement has been detected for a predetermined amount of time.

19. A monitor device for an ostomy appliance, the monitor device comprising:
- a housing;
- an accelerometer electrically coupled to the processor and configured to generate a position signal;
- an appliance interface for releasably coupling the monitor device to a sensor assembly of an ostomy appliance in a fixed position relative to the sensor assembly, the appliance interface comprising a plurality of terminals to electrically couple with a plurality of electrodes of the sensor assembly; and
- a processor arranged in the housing configured to determine, based on the position signal of the accelerometer, a spatial orientation of the monitor device relative to a stoma of a user.

20. The monitor device of claim 19, wherein the spatial orientation of the monitor device comprises a rotational offset relative to the stoma of the user.

21. The monitor device of claim 19, wherein the processor is configured to determine the spatial orientation relative based on a pattern of movement generated by the accelerometer.

22. The monitor device of claim 21, wherein the pattern of movement comprises a plurality of position signals sampled during a predefined amount of time.

23. The monitor device of claim 19, wherein the processor is configured to communicate an indication of the spatial orientation to an accessory device.

24. The monitor device of claim 19, wherein the processor is configured to entering a sleep mode if no movement has been detected for a predetermined amount of time.

* * * * *